United States Patent
Killeen et al.

(10) Patent No.: US 11,053,288 B2
(45) Date of Patent: Jul. 6, 2021

(54) ENHANCED PRODUCTION OF IMMUNOGLOBULINS

(71) Applicant: Trianni, Inc, San Francisco, CA (US)

(72) Inventors: Nigel Killeen, San Francisco, CA (US); Christoph Hasenhindl, San Francisco, CA (US); Bao Duong, San Francisco, CA (US)

(73) Assignee: TRIANNI, INC., San Francisco, CA (US)

(*) Notice: Subject to any disclaimer, the term of this patent is extended or adjusted under 35 U.S.C. 154(b) by 244 days.

(21) Appl. No.: 15/424,372

(22) Filed: Feb. 3, 2017

(65) Prior Publication Data

US 2017/0226162 A1     Aug. 10, 2017

Related U.S. Application Data

(60) Provisional application No. 62/291,217, filed on Feb. 4, 2016.

(51) Int. Cl.

| | | |
|---|---|---|
| *C07K 14/315* | (2006.01) | |
| *C07K 16/00* | (2006.01) | |
| *C07K 14/705* | (2006.01) | |
| *C07K 14/73* | (2006.01) | |
| *C07K 14/74* | (2006.01) | |
| *C12N 5/0781* | (2010.01) | |
| *C12N 5/12* | (2006.01) | |
| *C12N 5/16* | (2006.01) | |
| *A01K 67/027* | (2006.01) | |
| *C07K 16/42* | (2006.01) | |

(52) U.S. Cl.
CPC ........ *C07K 14/315* (2013.01); *A01K 67/0278* (2013.01); *C07K 14/70503* (2013.01); *C07K 14/70514* (2013.01); *C07K 14/70539* (2013.01); *C07K 14/70596* (2013.01); *C07K 16/00* (2013.01); *C07K 16/42* (2013.01); *C12N 5/0635* (2013.01); *C12N 5/12* (2013.01); *C12N 5/16* (2013.01); *A01K 2217/072* (2013.01); *A01K 2227/105* (2013.01); *A01K 2267/01* (2013.01); *C07K 2317/14* (2013.01); *C07K 2317/622* (2013.01); *C07K 2319/02* (2013.01); *C07K 2319/03* (2013.01); *C12N 2510/02* (2013.01)

(58) Field of Classification Search
CPC ...... C07K 14/315; C07K 16/42; C07K 16/00; C07K 14/70503; C07K 14/70596; C07K 14/70514; C07K 14/70539; C07K 2317/14; C07K 2319/03; C07K 2319/02; C07K 2317/622; C07K 14/705; C12N 5/16; C12N 5/0635; C12N 5/12; C12N 2510/02; A01K 67/0278; A01K 2217/072; A01K 2267/01; A01K 2227/105
See application file for complete search history.

(56) References Cited

U.S. PATENT DOCUMENTS

| | | |
|---|---|---|
| 4,892,824 A | 1/1990 | Skaletsky |
| 5,591,669 A | 1/1997 | Krimpenfort et al. |
| 5,593,598 A | 1/1997 | McGinness et al. |
| 5,612,205 A | 3/1997 | Kay et al. |
| 5,633,425 A | 5/1997 | Lonberg et al. |
| 5,661,016 A | 8/1997 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,955,300 A * | 9/1999 | Faure ................ C07K 16/2803 435/69.1 |
| 5,985,615 A | 11/1999 | Jakobovits et al. |
| 6,023,010 A | 2/2000 | Krimpenfort et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,162,963 A | 12/2000 | Kucherlapati et al. |
| 6,492,575 B1 | 12/2002 | Wagner et al. |
| 6,570,061 B1 | 5/2003 | Rajewsky et al. |
| 6,586,251 B2 | 7/2003 | Economides |
| 6,596,541 B2 | 7/2003 | Murphy |
| 6,653,113 B1 | 11/2003 | Berns et al. |
| 6,673,986 B1 | 1/2004 | Kucherlapati et al. |
| 6,998,514 B2 | 2/2006 | Bruggeman |
| 7,041,870 B2 | 5/2006 | Tomizuka et al. |
| 7,041,871 B1 | 5/2006 | Lonberg |
| 7,064,244 B2 | 6/2006 | Jakobovits et al. |

(Continued)

FOREIGN PATENT DOCUMENTS

| | | |
|---|---|---|
| CA | 2089661 C | 3/1992 |
| EP | 1399575 | 7/2006 |

(Continued)

OTHER PUBLICATIONS

Van Keuren et al., 2009, Transgenic Res., vol. 18(5), pp. 769-785 (Year: 2009).*
Ivies et al. (2014, Nature Protocols, vol. 9(4), pp. 810-827) (Year: 2014).*
West et al., 2016, J. Equine Vet. Sci., vol. 41, pp. 1-12 (Year: 2016).*
Meng et al. (2015, J. Animal Sci. and Biotech., pp. 1-7 (Year: 2015).*
Brevini et al., 2010, Theriogenology, vol. 74, pp. 544-550 (Year: 2010).*

(Continued)

*Primary Examiner* — Thaian N. Ton
(74) *Attorney, Agent, or Firm* — Medler Ferro Woodhouse & Mills PLLC

(57) ABSTRACT

The present invention provides methods and compositions for generating transgenic animals, including transgenic mammals, as well as plasma cells that allow for cell surface capture of secreted immunoglobulin molecules produced endogenously in the plasma cells.

13 Claims, 5 Drawing Sheets
Specification includes a Sequence Listing.

(56) References Cited

U.S. PATENT DOCUMENTS

| | | |
|---|---|---|
| 7,105,348 B2 | 9/2006 | Murphy |
| 7,129,084 B2 | 10/2006 | Buelow |
| 7,145,056 B2 | 12/2006 | Jakobovits |
| 7,148,040 B2 | 12/2006 | Meagher et al. |
| 7,205,148 B2 | 4/2007 | Economides et al. |
| 7,294,754 B2 | 11/2007 | Poueymirou et al. |
| 7,473,557 B2 | 1/2009 | Economides et al. |
| 7,476,536 B2 | 1/2009 | Kuroiwa et al. |
| 7,501,552 B2 | 3/2009 | Lonberg |
| 7,541,513 B2 | 6/2009 | Bruggeman |
| 7,659,442 B2 | 2/2010 | Poueymirou et al. |
| 7,868,223 B2 | 1/2011 | Tomizuka et al. |
| 8,158,419 B2 | 4/2012 | Lonberg |
| 8,163,546 B2 | 4/2012 | Akamatsu et al. |
| 8,232,449 B2 | 7/2012 | Tanamachi |
| 8,293,480 B2 | 10/2012 | Lonberg |
| 8,367,888 B2 | 2/2013 | Bruggeman |
| 8,502,018 B2 | 8/2013 | Murphy |
| 8,754,287 B2 | 6/2014 | MacDonald et al. |
| 9,012,717 B2 | 4/2015 | MacDonald et al. |
| 9,580,491 B2 | 2/2017 | Green et al. |
| 10,494,445 B2 | 12/2019 | Green et al. |
| 10,526,420 B2 | 1/2020 | Green et al. |
| 10,575,504 B2 | 3/2020 | Green et al. |
| 10,604,587 B2 | 3/2020 | Green et al. |
| 10,618,977 B2 | 4/2020 | Green et al. |
| 10,626,188 B2 | 4/2020 | Green et al. |
| 10,662,255 B2 | 5/2020 | Green et al. |
| 2003/0017534 A1 | 1/2003 | Buelow |
| 2006/0015957 A1 | 1/2006 | Lonberg |
| 2007/0061900 A1 | 3/2007 | Murphy |
| 2009/0055943 A1 | 2/2009 | Economides |
| 2009/0111126 A1 | 4/2009 | Akamatsu |
| 2009/0136950 A1 | 5/2009 | Dubridge |
| 2010/0317539 A1 | 12/2010 | Yu |
| 2011/0145937 A1 | 6/2011 | MacDonald et al. |
| 2011/0236378 A1 | 9/2011 | Green |
| 2011/0258710 A1 | 10/2011 | Murphy |
| 2011/0283376 A1 | 11/2011 | Murphy |
| 2012/0047585 A1 | 2/2012 | Rohrer et al. |
| 2012/0073004 A1 | 3/2012 | MacDonald |
| 2012/0090041 A1 | 4/2012 | Buelow |
| 2012/0096572 A1 | 4/2012 | MacDonald et al. |
| 2013/0137101 A1 | 5/2013 | Economides |
| 2013/0219535 A1 | 8/2013 | Wabl et al. |
| 2013/0263292 A1 | 10/2013 | Liang |
| 2013/0333057 A1 | 12/2013 | MacDonald et al. |
| 2014/0283153 A1 | 9/2014 | Trianni |
| 2015/0183820 A1 | 7/2015 | Honda et al. |
| 2017/0058052 A1 | 3/2017 | Wabl et al. |
| 2017/0188557 A1 | 7/2017 | Green et al. |
| 2017/0218090 A1 | 8/2017 | Green et al. |
| 2017/0303517 A1 | 10/2017 | Wabl |
| 2017/0306352 A1 | 10/2017 | Wabl |
| 2018/0230238 A1 | 8/2018 | Wabl et al. |
| 2020/0181285 A1 | 6/2020 | Green et al. |
| 2020/0181286 A1 | 6/2020 | Green et al. |
| 2020/0407464 A1 | 12/2020 | Green et al. |

FOREIGN PATENT DOCUMENTS

| | | | |
|---|---|---|---|
| EP | 1399559 | 4/2008 | |
| EP | 0817835 | 10/2008 | |
| EP | 2264163 | 12/2010 | |
| EP | 2517556 | 10/2012 | |
| EP | 2517557 | 10/2012 | |
| GB | 2398784 A | 9/2004 | |
| GB | 2561352 A | 10/2018 | |
| WO | 92/03918 A1 | 3/1992 | |
| WO | 94/25585 A1 | 11/1994 | |
| WO | WO-9530750 A2 * | 11/1995 | ....... C07K 14/70503 |
| WO | 96/40915 A2 | 12/1996 | |
| WO | 99/45962 A1 | 6/1999 | |
| WO | WO 11/004192 | 1/2001 | |
| WO | 01/09187 A2 | 2/2001 | |
| WO | WO 02/12437 | 2/2002 | |
| WO | 2002/057423 A2 | 7/2002 | |
| WO | 02/066618 A1 | 8/2002 | |
| WO | WO 02/066630 | 8/2002 | |
| WO | 2008/070367 A2 | 6/2008 | |
| WO | 2008/081197 A1 | 7/2008 | |
| WO | 2009/013620 A2 | 1/2009 | |
| WO | WO-2009033743 A1 * | 3/2009 | ............. A61P 25/28 |
| WO | 2009/157771 A2 | 12/2009 | |
| WO | 2010/005863 A1 | 1/2010 | |
| WO | 2010/039900 A2 | 4/2010 | |
| WO | 2011/123708 A2 | 10/2011 | |
| WO | WO 11/158009 | 12/2011 | |
| WO | WO 11/163311 | 12/2011 | |
| WO | WO 12/018610 | 2/2012 | |
| WO | 2012/123949 A1 | 9/2012 | |
| WO | 2013/022782 A1 | 2/2013 | |
| WO | 2013/092720 A1 | 6/2013 | |
| WO | 2013/138681 A1 | 9/2013 | |
| WO | 2013/171505 A2 | 11/2013 | |
| WO | 2014/013075 A2 | 1/2014 | |
| WO | 2015/112790 A2 | 7/2015 | |
| WO | 2015/188141 A2 | 12/2015 | |
| WO | 2017/035252 A1 | 3/2017 | |
| WO | 2017/095939 A1 | 6/2017 | |
| WO | 2018/189520 A1 | 10/2018 | |
| WO | 2020/074874 A1 | 4/2020 | |

OTHER PUBLICATIONS

Paris et al. (2010, Theriogenology, vol. 74, pp. 516-524) (Year: 2010).*

Munoz et al. (2008, Theriogenology, vol. 69, pp. 1159-1164) (Year: 2008).*

Gomez et al. (2010, Theriogenology, vol. 74, pp. 498-515) (Year: 2010).*

Buta et al. (2013, Stem Cell Res., vol. 11, pp. 552-562) (Year: 2013).*

Tong et al. (2010, Nature, vol. 467(7312), pp. 211-213) (Year: 2010).*

Hong et al. (2012, Stem Cells and Development, vol. 21(9), pp. 1571-1586) (Year: 2012).*

2004, Barthold S., Genetica, vol. 122, pp. 75-88, see p. 85 col. 2 parag. 2 lines 1-13). (Year: 2004).*

Choe et al., 2016, Materials, vol. 9, pp. 1-17 (Year: 2016).*

Garcia-Arocena D. (2014, The Jackson Laboratory, Same Mutation, Different Phenotype?) (Year: 2014).*

Heimain-Patterson et al. (2011, Amyotrophic Lateral Schlerosis, vol. 00, pp. 1-8) (Year: 2011).*

Ait-Azzouzene et al., Journal of Experimental Medicine, vol. 201, No. 5, Mar. 7, 2005 817-828.*

Cheng TL, Roffler S. Membrane-tethered proteins for basic research, imaging, and therapy. Med Res Rev. Nov. 2008;28(6):885-928.*

Young et al., Biotechnol. J., 7: 620-634, 2012.*

Burckstrummer et al., Nature Methods, 3(12): 1013-1019, 2006.*

Guss et al., The EMBO Journal vol. 5 No. 7 pp. 1567-1575, 1986.*

Lee et al., Cancer Biol. Ther. 8 (2), 161-166 (2009).*

Tunyaplin et al., Nucleic Acids Research, 2000, vol. 28, No. 24, 4846-4855.*

Melidoni et al., PNAS, 110(44): 17802-17807, 2013.*

Lanitis, Cancer Immunol Res; 1(1); 43-53, 2013.*

Debono, et al., "Vh Gene Segments in the Mouse and Human Genomes", J. Mol. Biol., 342:131-34 (2004).

Wallace, et al., "Manipulating the Mouse Genome to Engineer Precise Functional Syntenic Replacements with Human Sequence", Cell, 128:197-209 (2007).

Zhang, et al., ":A New and Robust Method of Tethering IgG Surrogate Antigens on Lipid Bilayer Membranes to Facilitate the TIRFM Based Live Cell and Single Molecule Imaging Experiments", PLOS One, 8(5):e63735 (2013).

Altschul et al., "Basic local alignment search tool," *J Mol Biol* 215:403-410 (1990).

Avitahl et al., "A 125 bp region of the Ig $V_H1$ promoter is sufficient to confer lymphocyte-specific expression in transgenic mice," *Int Immunol* 8(9):1359-1366 (1996).

(56) References Cited

OTHER PUBLICATIONS

Bentley et al., "Unrearranged immunoglobulin variable region genes have a functional promoter," *Nucleic Acids Res* 10:1841-1856 (1982).
Berman et al., "Content and organization of the human Ig $V_H$ locus: definition of three new $V_H$ families and linkage to the Ig $C_H$ locus," *EMBO J* 7(3):727-738 (1988).
Blankenstein et al., "Immunoglobulin $V_H$ region genes of the mouse are organized in overlapping cluster," *Eur J Immunol* 17:1351-1357 (1987).
Brekke et al., "Assembly and analysis of the mouse immunoglobulin kappa gene sequence," *Immunogenetics* 56:490-505 (2004).
Bruggemann, "The Preparation of Human Antibodies from Mice Harbouring Human Immunoglobulin Loci," *Transgenic Animals: Generation and Use*, pp. 397-402, Ed. L.M. Houdebine, CRC Press (1997).
Casellas et al., "Igk allelic inclusion is a consequence of receptor editing," *J Exp Med* 204(1):153-160 (2007).
Cesari et al, "Elk-1 knock-out mice engineered by Flp recombinase-mediated cassette exchange," *Genesis* 38:87-92 (2004).
Church et al., "Lineage-specific biology revealed by a finished genome assembly of the mouse," *PLoS Biol* 7:e1000112 (2009).
Clarke et al., "An immunoglobulin promoter region is unaltered by DNA rearrangement and somatic mutation during B-cell development," *Nucleic Acids Res* 10:7731-7749 (1982).
Decaire et al., "A Publicly Available PCR Methods Laboratory Manual and Supporting Material," *J Microbiol Biol Educ* 16:269-270 (2015).
Downing et al., "Technical assessment of the first 20 years of research using mouse embryonic stem cell lines," *Stem Cells* 22:1168-1180 (2004).
Doyen et al., "Analysis of promoter and enhancer cell type specificities and the regulation of immunoglobulin gene expression," *Gene* 50:321-331 (1986).
Featherstone et al., "The Mouse Immunoglobulin Heavy Chain V-D Intergenic Sequence Contains Insulators That May Regulate Ordered V(D)J Recombination," *J Biol Chem* 285:9327-9338 (2010).
Fishwild et al., "High-avidity human IgG kappa monoclonal antibodies from a novel strain of minilocus transgenic mice," *Nat Biotechnol*, 14:845-851 (1996).
Gellert, "Molecular analysis of V(D)J recombination," *Annu Rev Genet* 26:425-446 (1992).
Gopal et al., "Contribution of promoter to tissue-specific expression of the mouse immunoglobulin kappa gene," *Science* 229:1102-1104 (1985).
Hengartner et al., "Assignment of genes for immunoglobulin kappa and heavy chains to chromosomes 6 and 12 in mouse," *Proc Natl Acad Sci USA* 75:4494-4498 (1978).
Honjo et al., ed. *Immunoglobulin Genes*. San Diego, CA: Academic Press Inc., 1989; Chapters 4-6 and 17.
Ichihara et al., "Organization of human immunoglobulin heavy chain diversity gene loci," *EMBO J* 7(13):4141-4150 (1988).
International Human Genome Sequencing Consortium, "Finishing the euchromatic sequence of the human genome," *Nature* 431:931-945 (2004).
Johnston et al., "Complete Sequence Assembly and Characterization of the C57BL/6 Mouse Ig Heavy Chain V Region," *J Immunol* 176:4221-4234 (2006).
Jones et al., "Replacing the complementarity-determining regions in a human antibody with those from a amouse," *Nature* 321:522-525 (1986).
Jung et al., "Unraveling V(D)J Recombination: Insights into Gene Regulation," *Cell* 116:299-311 (2004).
Kabat et al., "Variable region genes for the immunoglobulin framework are assembled from small segments of DNA—A hypothesis," *Proc Natl Acad Sci USA* 75:2429-2433 (1978).
Kabat et al., "Evidence supporting somatic assembly of the DNA segments (minigenes), coding for the framework, and complementarity-determining segments of immunoglobulin variable regions," *J Exp Med* 149:1299-1313 (1979).

Kawasaki et al., "One-Megabase Sequence Analysis of the Human Immunoglobulin λ Gene Locus," *Genome Res* 7:250-261 (1997).
Kitamura et al., "Targeted disruption of μ chain membrane exon causes loss of heavy-chain allelic exclusion," *Nature* 356:154-156 (1992).
Kozak, "An analysis of 5'-noncoding sequences from 699 vertebrate messenger RNAs," *Nucleic Acids Res* 15:8125-8148 (1987).
Kurosawa et al., "Organization, Structure, and Assembly of Immunoglobulin Heavy Chain Diversity *DNA* Segments," *J Exp Med* 155:201-218 (1982).
Lander et al., "Initial sequencing and analysis of the human genome," *Nature* 2001, 409:860-921 (2001).
Landsteiner et al., "On the Specificity of Serological Reactions with Simple Chemical Compounds (Inhibition Reactions)," *J Exp Med* 54:295-305 (1931).
Lee et al., "Genome data mining for everyone," *BMB Reports* 41(11):757-764 (2008).
Lefranc et al., "IMGT unique numbering for immunoglobulin and T cell receptor variable domains and Ig superfamily V-like domains," *Dev Comp Immunol* 27:55-77 (2003).
Lutz et al., "Pro-B cells sense productive immunoglobulin heavy chain rearrangement irrespective of polypeptide production," *Proc Nat Acad Sci USA* 108(26):10644-10649 (2011).
Mason et al., "Transcription cell type specificity is conferred by an immunoglobulin VH gene promoter that includes a functional consensus sequence," *Cell* 41:479-487 (1985).
Matsuda et al., "The Complete Nucleotide Sequence of the Human Immunoglobulin Heavy Chain Variable Region Locus," *J Exp Med* 188(11):2151-2162 (1998).
Misra et al., "Gene targeting in the mouse: advances in introduction of transgenes into the genome by homologous recombination," *Endocrine* 19:229-238 (2002).
Mouse Genome Sequencing Consortium, "Initial sequencing and comparative analysis of the mouse genome," *Nature* 420:520-562 (2002).
Ristevski, "Making better transgenic models: conditional, temporal, and spatial approaches," *Mol Biotechnol* 29:153-163 (2005).
Roebroek et al., "Mutant Lrp1 knock-in mice generated by recombinase-mediated cassette exchange reveal differential importance of the NPXY motifs in the intracellular domain of LRP1 for normal fetal development," *Mol Cell Biol* 26:605-616 (2006).
Saiki et al., "Analysis of enzymatically amplified beta-globin and HLA-DQ alpha DNA with allele-specific oligonucleotide probes," *Nature* 324:163-166 (1986).
Sakano et al., "Identification and nucleotide sequence of a diversity DNA segment (D) of immunoglobulin heavy-chain genes," *Nature* 290:562-565 (1981).
Schellenberg et al., "Pre-mRNA splicing: a complex picture in higher definition," *Trends Biochem Sci* 33:243-246 (2008).
Sharon, "The invariant tryptophan in an H chain V region is not essential to antibody binding," *J Immunol* 140:2666-2669 (1988).
Tonegawa, "Somatic generation of antibody diversity," *Nature* 302:575-581 (1983).
Toor et al., "Structural insights into RNA splicing," *Curr Opin Struct Biol* 19:260-266 (2009).
Venter et al., "The sequence of the human genome," *Science* 291:1304-1351 (2001).
Von Heijne, "Protein targeting signals," *Curr Opin Cell Biol* 2:604-608 (1990).
Xiong et al., "Chemical gene synthesis: strategies, softwares, error corrections, and applications," *FEMS Microbiol Rev* 32:522-540 (2008).
International Preliminary Report on Patentability dated Aug. 7, 2018 in corresponding International Patent Application No. PCT/US2017/016521.
Gunasekaran et al., "Enhancing Antibody Fc Heterodimer Formation through Electrostatic Steering Effects," *J Biol Chem* 285:19637-19646 (2010).
Liu et al., "A Novel Antibody Engineering Strategy for Making Monovalent Bispecific Heterodimeric IgG Antibodies by Electrostatic Steering Mechanism," *J Biol Chem* 290:7535-7362 (2015).
Ma et al., "DNA Synthesis, Assembly and Applications in Synthetic Biology," *Curr Opin Chem Biol* 16:260-267 (2012).

(56) References Cited

OTHER PUBLICATIONS

McLenachan et al., "Flow-cytometric analysis of mouse embryonic stem cell lipofection using small and large DNA constructs," *Genomics* 89:708-720 (2007).
Rajewsky et al., "Allelic exclusion model questioned," Scientific Correspondence, *Nature* 359:371-372 (1992).
Sonoda et al, "B Cell Development under the Condition of Allelic Inclusion," *Immunity* 6:225-233 (1997).
Vetterman et al., "Allelic exclusion of immunoglobulin genes: models and mechanisms," *Immunol Rev* 237:22-42 (2010).
Wabl et al., "Allelic exclusion model questioned," Scientific Correspondence, *Nature* 359:370-371 (1992).
Clargo et al., "The rapid generation of recombinant functional monoclonal antibodies from individual, antigen-specific bone marrow-derived plasma cells isolated using a novel fluorescence-based method," *mAbs* 6(1): 143-159 (2013).
Kontermann et al., "Bispecific antibodies," *Drug Discov Today* 20(7):838-847 (2015).
Li et al., "Biochemical Analysis of the Regulatory T Cell Protein Lymphocyte Activation Gene-3 (LAG-3; CD223)," *Journal of Immunology* 173: 6806-6812 (2004).
Manz et al., "Analysis and sorting of live cells according to secreted molecules relocated to a cell-surface affinity matrix," *Proceedings of the National Academy of Science USA* 92: 1921-1925 (1995).
Pinder et al., "Isolation and Characterization of Antigen-Specific Plasmablasts Using a Novel Flow Cytometry-Based Ig Capture Assay," *Journal of Immunology* 199(12): 4180-4188 (2017).
Price et al., "Engineered cell surface expression of membrane immunoglobulin as a means to identify monoclonal antibody-secreting hybridomas," *Journal of Immunological Methods* 343: 28-41 (2009).
Verkoczy et al., "Human Ig knockin mice to study the development and regulation of HIV-1 broadly neutralizing antibodies," *Immunol. Rev.* 275:89-107 (2017).
Zhou et al., "Generation of Monoclonal Antibodies against Highly Conserved Antigens," *PLoS One* 4(6):e6087 (2009).
Notice of Reason for Rejection dated Apr. 7, 2020 in corresponding Japanese Patent Application No. 2018-560448.
U.S. Appl. No. 61/361,302, filed Jul. 2, 2010 in the name of ABLEXIS, LLC.
U.S. Appl. No. 61/319,690, filed Mar. 31, 2010 in the name of ABLEXIS, LLC.
Martin, Jolyon et al., "Comprehensive annotation and evolutionary insights into the canine (*Canis lupus* familiaris) antigen receptor loci", Immunogenetics, 2018, vol. 70, pp. 223-236.
Third-Party Submission dated Mar. 31, 2021 in U.S. Appl. No. 16/849,347, filed Apr. 15, 2020.
Communication dated Apr. 2, 2021 regarding Third Party Submission.
Proudhon, Charlotte et al., "Long Range Regulation of V(D)J Recombination", Adv Immunol., 2015, vol. 128, pp. 123-182.
Ramsden, Dale A. et al., "Conservation of sequence in recombination signal sequence spacers", Nucleic Acids Research, 1994, vol. 22, No. 10, pp. 1785-1796.
Office Action issued Aug. 22, 2019 in U.S. Appl. No. 15/603,334.
Amendment/Reply under 37 C.F.R § 1.111 filed Sep. 19, 2019 in response to the Non-Final Office Action dated Aug. 22, 2019 in U.S. Appl. No. 15/603,334.
Amendment/Reply under 37 C.F.R § 1.114 filed Jul. 10, 2017 in response to the Final Office Action: dated Feb. 24, 2017 in U.S. Appl. No. 13/818,184.

\* cited by examiner

ENHANCED PRODUCTION OF IMMUNOGLOBULINS

RELATED APPLICATION

This application claims priority to U.S. Ser. No. 62/291,217, filed Feb. 4, 2016.

FIELD OF THE INVENTION

This invention relates to production of immunoglobulin molecules, including methods for rapid screening of antigen-specific antibody-secreting cells for the generation of monoclonal antibodies.

BACKGROUND OF THE INVENTION

In the following discussion certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Monoclonal antibodies are important biologics that have been widely employed in biomedical research, in clinical diagnostics, and as therapeutic agents because of their exquisite ability to bind antigens of diverse molecular forms. In drug development, monoclonal antibodies are often the molecules of choice because they exhibit desirable pharmacokinetics that are associated with powerful immunological functions normally involved in fending off infectious agents. Furthermore, laboratory animals can readily mount a specific antibody response against any target molecule that is not present natively in the body, making antibody generation a relatively low-risk and cost-efficient approach when compared to alternative strategies.

Although hybridoma technology was developed more than four decades ago, today it is still the most widely employed technique to generate antigen-specific monoclonal antibodies. In this approach, an animal (typically, a rodent or a rabbit) is first immunized with an antigen of interest. B lymphocytes in the immunized animal that have the receptor specificity for the antigen then become activated, clonally expand, and differentiate into antibody-secreting cells (ASCs). The immunized animal is then sacrificed, and because the ASCs isolated from these animals cannot survive indefinitely in culture, these cells are often immortalized by fusion with malignant plasma cells (such as myeloma or plasmacytoma cells) to generate hybrid cells called hybridomas. The hybridoma cells are then screened and selected for their ability to secrete antibodies with reactivity to the antigen of interest, often involving multiple rounds of limiting dilution and propagation in culture.

Alternatively, the ASCs can be individually sorted, and the genes encoding the heavy chain and light chain variable domains ($V_H$ and $V_L$, respectively) directly cloned without the need to propagate the ASCs in vitro. The $V_H$- and $V_L$-encoding DNA fragments are next subcloned into an expression vector containing exon sequences for the desired heavy chain and light chain constant regions, respectively. Each $V_H$ and $V_L$ pair of expression vectors are then transfected into a cell line to express the monoclonal antibodies, which are subsequently screened for their ability to recognize the antigen of interest.

Despite the eventual success in producing monoclonal antibodies against the antigen of interest using either hybridoma or single-cell cloning technique, the efficiency of both techniques is hampered by the labor-intensive process of screening and selection. This is because it has not been feasible to pre-select only the antigen-specific ASCs for fusion with myeloma cells or for single-cell cloning. When B lymphocytes differentiate into ASCs in response to an antigenic encounter, the membrane-bound form of antigen receptors is down-regulated in favor of the secreted form. Thus, selection methods based on the cell surface expression of antigen receptors, such as magnetic or flow-cytometric sorting, do not work well as tools to select for antigen-specific ASCs. Due to this lack of ability to pre-select ASCs, only a small fraction of cells screened in both hybridoma and single-cell cloning techniques produces monoclonal antibodies with specificity for the antigen of interest.

U.S. Pat. No. 7,148,040 B2 provides methods to express the membrane-bound form of antigen receptors on hybridoma cells to improve the efficiency of hybridoma screening by selection techniques based on the cell surface expression of antigen receptors. In this approach, myeloma cells are transfected with expression constructs encoding CD79A and CD79B, also known as Igα and Igβ, respectively. CD79A and CD79B are expressed as heterodimers that are necessary for both cell surface expression and signaling functions of the antigen receptors on B cells. As B lymphocytes differentiate into ASCs, they down-regulate CD79A and CD79B expression, thus contributing to the loss of antigen receptor expression on the cell surface. Therefore, re-introducing the expression of CD79A and CD79B allows for increased representation of the membrane-bound form of antigen receptors on the hybridomas. Although this strategy helps reduce the labor of hybridoma screening and selection, the efficiency could be greatly improved if it was feasible to pre-select only the antigen-specific ASCs for fusion with myeloma cells. Moreover, the specified methods do not provide a strategy to increase the efficiency of monoclonal antibody generation using direct $V_H$ and $V_L$ cloning technique from sorted single cells.

Re-introduction of CD79A and CD79B expression by ASCs in vivo may not provide a viable strategy to increase the expression of antigen receptors on the cell surface either. Because CD79A and CD79B expression is tightly regulated during B lymphocyte development, alterations in their expression levels in vivo may have profound consequences on B lymphocyte survival, functions, and/or antigen receptor selection. Moreover, the antigen receptors on ASCs are likely to be internalized at the time of ASC isolation due to their active engagement with the immunogen, since the immune response is still ongoing when the mouse is euthanized. If instead, signaling-deficient mutant CD79A and CD79B are expressed on ASCs to prevent antigen receptor internalization, it remains unexplored whether the mutant forms of these molecules exhibit a dominant-negative effect that negatively impacts ASC survival and functions in vivo. Finally, expressing CD79A and CD79B on ASCs ex vivo to circumvent the aforementioned problems associated with their enforced expression in vivo is not a practical strategy because ASCs are not amenable to gene transfer by most methods currently available.

Thus, a method for more efficient screening for antigen-specific ASCs is an important unmet need. The methods and compositions provided by the present specification meet this important need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides methods and compositions for enhanced production of immunoglobulin molecules. Specifically, the invention provides methods and compositions for the capture of secreted immunoglobulin molecules, including those of IgG, IgA, IgE and IgM isotypes, at the surface of ASCs. The present invention also comprises transgenic animals, including transgenic mammals, comprising engineered ASCs that can capture and display on their cell surface immunoglobulin molecules produced endogenously from within the ASCs.

In one embodiment, the invention provides restricted constitutive expression of an engineered immunoglobulin-capturing molecule comprising one or more immunoglobulin-binding portions or domains derived from bacterial protein(s) such as Protein A and/or Protein G, using an expression system that expresses the immunoglobulin-capturing molecule preferentially on ASCs with minimal expression at the stages of B cell development prior to antigen-induced differentiation.

In another embodiment, the invention provides restricted constitutive expression of an engineered immunoglobulin-capturing molecule comprising a single-chain antibody with specificity to an immunoglobulin, using an expression system that expresses the immunoglobulin-capturing molecule preferentially on ASCs with minimal expression at the stages of B cell development prior to antigen-induced differentiation.

The engineered ASCs express immunoglobulin-capturing molecules that are tethered to the cell surface and have the ability to selectively bind immunoglobulin molecules (also, as used herein "immunoglobulins" or "antibodies") with sufficient affinity to immobilize the immunoglobulin molecules at the plasma membrane. Because ASCs secrete thousands of immunoglobulin molecules per second, the immunoglobulin-capturing molecules on a given ASC are saturated primarily with the immunoglobulin molecules secreted by that ASC rather than with immunoglobulins secreted by other ASCs. Expression of genes encoding cell surface immunoglobulin-capturing molecules provides a means for identifying ASCs based on the particular monoclonal immunoglobulin molecules being expressed.

In certain aspects, the immunoglobulin-capturing molecule is tethered to the membrane by a peptide sequence derived from a transmembrane protein such as but not limited to human Lymphocyte-Activation Gene 3 (LAG3). In other aspects, the immunoglobulin-capturing molecule is tethered to the plasma membrane via a post-translational modification with, e.g., glycosylphosphatidylinositol (GPI). In some of these aspects, the immunoglobulin-capturing molecule further comprises a long stalk for support, flexibility, and extended protrusion into the extracellular space.

In certain aspects, expression of the immunoglobulin-capturing molecules is driven by a promoter derived from a human or mouse gene that is highly expressed in ASCs developed in vivo or in vitro. In other aspects, the immunoglobulin-capturing molecules are expressed by an inducible system, such as the tetracycline system, in vivo or in vitro. In some aspects, expression of the immunoglobulin-capturing molecule is coupled to the expression of a reporter gene, such as green fluorescent protein (GFP), via an internal ribosomal entry site sequence (IRES) or a picornavirus 2A ribosomal skip sequence in the expression vector.

The present invention also provides methods for generating a non-human transgenic animal expressing immunoglobulin-capturing molecules on ASCs. The methods comprise introducing an immunoglobulin-capturing molecule-encoding gene into the genome of a non-human vertebrate, wherein the introduced gene provides constitutive or inducible expression of the immunoglobulin-capturing molecule on host ASCs. In some aspects the transgenic animal is a rodent, preferably a mouse. In other aspects, the transgenic animal is avian, preferably a chicken. In particularly preferred aspects, the transgenic animal is a mouse that expresses human genes encoding the variable domains of the heavy and light chains and lacks the mouse versions of these genes; for example, as described in US Pub. No. 2013/0219535, which is incorporated by reference in its entirety.

The invention additionally provides processes for isolating genes that encode immunoglobulins of a particular specificity from ASCs that display the specific immunoglobulins captured on the surface of the ASCs.

The present invention also provides libraries for identification of antibodies of interest from the engineered cells of the invention. The antibody libraries produced using the methods and compositions of the invention provide a facilitated means for the screening and production of antibodies that selectively bind to a target of interest. Such libraries thus enhance the isolation of monoclonal antibodies for use in the clinical, diagnostic, and research settings.

An advantage of the invention is that the determination of immunoglobulin specificity can be made using established techniques such as binding to fluorescently labeled antigen and flow cytometric or microscopic procedures. Such procedures allow for enhanced efficiency in identification and isolation of rare antigen-specific cells and the cloning of the rearranged immunoglobulin genes from the isolated cells.

These and other aspects, objects and features are described in more detail below.

DEFINITIONS

Figure 1C:
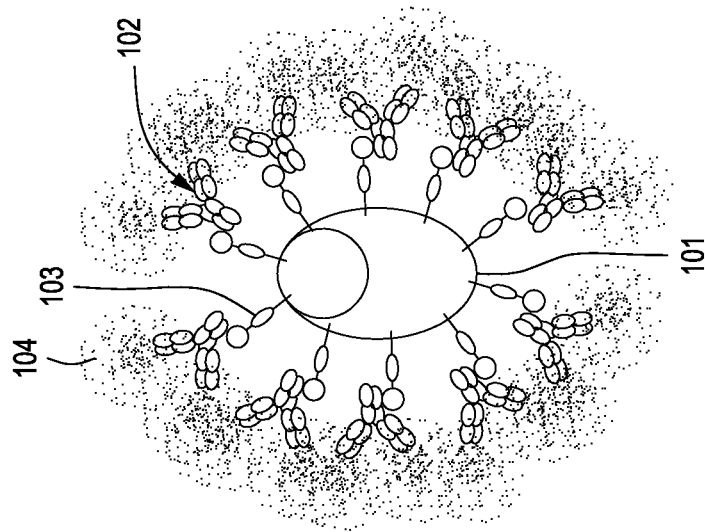
FIGS. 1A, 1B and 1C are illustrations of a secreting ASC with no immunoglobulin-capturing molecules on the cell surface (FIG. 1A), an ASC with immunoglobulin-capturing molecules and captured immunoglobulin molecules (i.e., antibodies) on the surface of the ASC (FIG. 1B), and the binding of labeled antigens to the antibodies retained by the immunoglobulin-capturing molecules expressed on an ASC (FIG. 1C).

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

An "antibody-secreting cell" or "ASC" refers to a cell that has differentiated from an antigen-experienced B cell and acquired the capacity to express as well as secrete large amounts of immunoglobulin molecules. ASCs include plasmablasts and short-lived or long-lived plasma cells in the animal, as well as plasmablasts and plasma cells developed in vitro from B cell cultures.

A "capture molecule" is any moiety that contains a region that selectively binds to a part of or a whole molecule of interest.

"Capture" refers to selective binding and immobilization of a molecule at a cell surface due to a durable interaction between that molecule and a membrane-bound capture molecule.

"Cell surface" refers to the plasma membrane of a cell, i.e., that part of a cell most directly exposed to extracellular spaces and available for contact both with cells and proteins in the extracellular (including intercellular) space.

An "immature B cell" refers to a cell at an intermediate phase of B cell differentiation, during which a hematopoietic stem cell undergoes genetic programming to become a mature, yet antigen-inexperienced, B cell. A "mature" B cell refers to an antigen-inexperienced B cell, which is capable of clonal expansion, as well as differentiation into a memory cell or an antibody-secreting cell, upon activation by an antigen.

An "immunoglobulin" refers to an antibody, whether a part of or whole antibody molecule. In most vertebrate animals including humans, antibodies normally exist as dimers of two identical heavy (H) chains that are each paired with an identical light (L) chain. The N-termini of both H and L chains consist of a variable domain ($V_H$ and $V_L$, respectively) that together provide the H-L pair with its unique antigen-binding specificity. The constant region of the H chain consists of 3 to 4 immunoglobulin domains (referred to as $C_H1$ to $C_H4$) with or without a hinge, depending on the isotype (or antibody class). In mice, the isotypes are IgM, IgD, IgG3, IgG1, IgG2b, IgG2a or IgG2c, IgE, and IgA. The light chain constant region consists of either a κ or λ immunoglobulin domain (referred to as Cκ or Cλ). In both mice and humans, the presence of κ light chains predominates over that of λ light chains in the total pool of immunoglobulins within an individual. In certain mammals, such as camelids or animals made deficient in light chain expression, immunoglobulins may consist of heavy chains only. Despite the lack of light chains, these immunoglobulins are also efficiently retained on the cell surface by immunoglobulin-capturing molecules designed to bind to the immunoglobulin heavy chain described in the present invention. Additionally, an immunoglobulin can refer to an unconventional antibody, whether in part or in whole, such as a bispecific antibody that consists two or more $V_H$ and/or $V_L$ domains, for example, as described in U.S. Ser. No. 15/246,181, filed 24 Aug. 2016, which is incorporated by reference in its entirety. Finally, an immunoglobulin also refers to a hybrid molecule consisting of part of an antibody, particularly the antibody constant region, and part of another protein. The immunoglobulin-capturing molecules described in the present invention also may be designed and engineered to retain hybrid immunoglobulin molecules for display at the cell surface.

An "immunoglobulin-capturing molecule" refers to a plasma membrane-bound molecule that can bind, retain, and display immunoglobulin molecules (i.e., immunoglobulins or antibodies) at the cell surface.

An "immunoglobulin superfamily" or "IgSF" molecule refers to a molecule that possesses immunoglobulin folds (Ig folds) that are structurally similar to the immunoglobulin domains found in antibody molecules.

The term "transgene" is used herein to describe genetic material which has been or is about to be artificially inserted into the genome of a cell.

"Transgenic animal" refers to a non-human animal, usually a mammal such as a rodent, particularly a mouse or rat although other animals are envisioned, having an exogenous nucleic acid sequence present as a chromosomal or extra-chromosomal element in a portion of its cells or stably integrated into its germ-line DNA (i.e., in the genomic sequence of most or all of its cells).

A "vector" or "expression construct" includes plasmids and viruses and any DNA or RNA molecule, whether self-replicating or not, which can be used to transform, transduce, or transfect a cell.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999) *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2007), *PCR Primer: A Laboratory Manual*; Sambrook and Russell (2006), *Condensed Protocols from Molecular Cloning: A Laboratory Manual*; and Green and Sambrook (2012), *Molecular Cloning: A Laboratory Manual* (all from Cold Spring Harbor Laboratory Press); Stryer, L. (1995) *Biochemistry* (4th Ed.) W.H. Freeman, New York N.Y.; Lehninger, *Principles of Biochemistry* 3rd Ed., W. H. Freeman Pub., New York, N.Y.; and Berg et al. (2002) *Biochemistry*, 5th Ed., W.H. Freeman Pub., New York, N.Y.; Nagy, et al., Eds. (2003) *Manipulating the Mouse Embryo: A Laboratory Manual* (3rd Ed.) Cold Spring Harbor Laboratory Press, Cold Spring Harbor, N.Y., *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); and *Mammalian Chromosome Engineering—Methods and Protocols* (G. Hadlaczky, ed., Humana Press 2011), all of which are herein incorporated in their entirety by reference for all purposes.

Note that as used herein and in the appended claims, the singular forms "a," "an," and "the" include plural referents unless the context clearly dictates otherwise. Thus, for example, reference to "an immunoglobulin" refers to one or more such immunoglobulins, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

THE INVENTION IN GENERAL

Antibody-secreting cells (ASCs) normally do not display the immunoglobulins they express and secrete on their plasma membrane, making highly advanced techniques based on cell surface labeling, such as magnetic and flow-cytometric sorting, inapplicable as methods to select for antigen-specific ASCs. The present invention was born out of the need for a system that allows for efficient screening of ASCs based on cell surface presentation of secreted immunoglobulin molecules (also as used herein "immunoglobulins" or "antibodies"). Specifically, the present invention provides a means for expressing immunoglobulin-capturing molecules that can retain and immobilize immunoglobulins at the surface of the secreting cells, such as ASCs or hybridomas, which do not normally express high levels of membrane-bound immunoglobulins or naturally have the ability to retain immunoglobulins on their cell surface. ASCs express and release large amounts of immunoglobulins (thousands of molecules per second) (see, e.g., Mitchell, *Advances in Immunology* 28:451-511 (1979)). Therefore, the immunoglobulin-capturing molecules expressed on these cells are saturated primarily with immunoglobulins produced from within, rather than with the immunoglobulins secreted by other cells. Thus, the immunoglobulin-capturing molecules must possess a high affinity and a low dissociation rate for the immunoglobulin molecules they capture. The present invention provides methods and compositions for expression of such high-affinity immunoglobulin-capturing molecules with low dissociation rates.

Engineering ASCs to capture endogenously produced immunoglobulins on their cell surface provides a facile means for discriminating the antigen specificity of the antibodies that each ASC produces, and for separating ASCs secreting desired immunoglobulins from those ASCs that do not. Discrimination can be accomplished by, e.g., using antigens labeled with substances that facilitate identification and purification of cells (e.g., magnetic, biotinylated, fluorescent, radioactive, or enzymatic molecules) by well-established procedures known in the art.

Figure 1B:
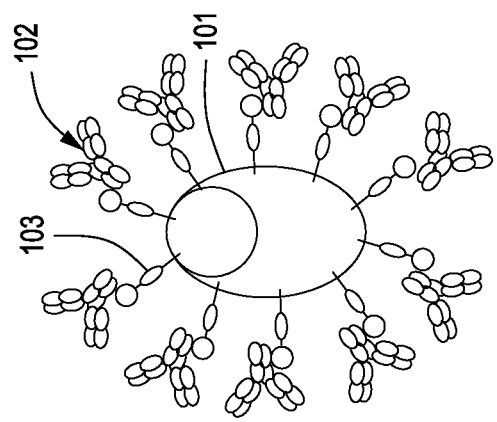
Figure 1A:
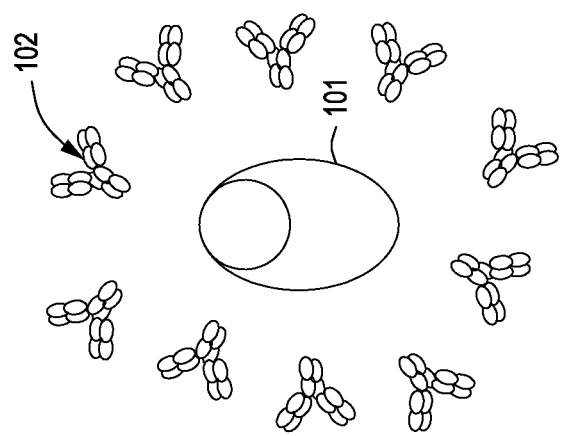

FIGS. 1A, 1B and 1C illustrate the principles of the present invention in one exemplary embodiment. As depicted in FIG. 1A, an antibody-secreting cell (ASC) (101) does not normally express the membrane-bound form of the immunoglobulin molecule, nor does it retain the secreted form of the immunoglobulin molecule (i.e., antibody) (102) on its cell surface. The present invention provides methods and compositions for the expression of immunoglobulin-capturing molecules (103) on the cell surface of ASCs. According to the invention, during the synthesis of the immunoglobulin molecules in the endoplasmic reticulum and subsequent packaging in the vesicles for secretion—or soon after their secretion—some immunoglobulin molecules (102) are retained on the cell surface by immunoglobulin-capturing molecules (103) as depicted in FIG. 1B. Labeled antigens (104) (e.g., fluorescently-labeled antigens) are then allowed to bind to the immunoglobulin molecules (antibodies) (102) that have bound to an immunoglobulin-binding portion of the immunoglobulin-capturing molecules (103) on the cell surface of the ASC, as depicted in FIG. 1C. Antigen-specific ASCs are then identified by the labeled antigens (104) bound to the immunoglobulin-binding portion of the immunoglobulin-capturing molecules (102) that have been captured on the cell surface. Detection of antigen binding on the ASCs is accomplished by, e.g., using antigens that are directly labeled with a fluorophore or other reporter molecule. The ASCs that bind labeled antigens are then purified by, e.g., cell-sorting techniques known in the art.

The purified ASCs expressing antibodies specific for a particular antigen may then be immortalized by fusion with myeloma or plasmacytoma cells, or directly used as a source of nucleic acids (DNA or mRNA) for the creation of libraries of sequences encoding immunoglobulins.

Libraries from purified ASCs contain rearranged immunoglobulin genes encoding antibodies of defined specificity (i.e., specificity for the antigens used in the purification process). The $V_H$ and $V_L$ genes can be identified from the antigen-specific ASCs by deep sequencing coupled with bioinformatics data mining (see, e.g., Haessler and Reddy, Methods in Molecular Biology 1131:191-203 (2014)). Alternatively, the antigen-specific ASCs can be individually sorted. The $V_H$ and $V_L$ domains unique to each ASC are then cloned via established RT-PCR or 5' Rapid Amplification of cDNA Ends (5' RACE) techniques adapted to single-cell cloning (for review, see, e.g., Tiller, et al., New Biotechnology 5:453-7 (2011)). In yet another alternative, the $V_H$ and $V_L$ sequences can be identified using the methods and materials described in U.S. Pat. Nos. 9,328,172; 8,309,035; and 8,309,317.

The Immunoglobulin-Capturing Molecule

The immunoglobulin-capturing molecules of the present invention that are expressed at the cell surface comprise at least two components, and in preferred embodiments may comprise additional components, as described in detail below. In a simple form, the immunoglobulin-capturing molecules comprise a cell surface tether component, and an immunoglobulin-binding component. The cell surface tether component may comprise a transmembrane peptide domain that tethers or anchors the expressed immunoglobulin-binding component in the cell surface membrane, or the cell surface tether component may comprise a chemical moiety (for example, glycosylphosphatidylinositol) that allows for the immunoglobulin-binding component to be tethered to the cell surface membrane via a chemical bond. In addition to these components, the immunoglobulin-capturing molecules of the present invention may comprise a stalk component, one or more linker components, and/or a reporter peptide.

In one embodiment, the immunoglobulin-capturing molecule consists of one or more immunoglobulin-binding domains or portions derived from one or more bacterial proteins that naturally have affinity for the constant region of the heavy or light chain of immunoglobulins. Such immunoglobulin-binding proteins include but are not limited to Protein A from *Staphylococcus aureus*, Protein G from group C and G Streptococci, Protein H from *Streptococcus pyogenes*, or Protein L from *Peptostreptococcus magnus*. In some embodiments, the immunoglobulin-capturing molecule is expressed as a hybrid molecule comprising two or more immunoglobulin-binding domains derived from two or more different bacterial proteins. As an example, the capture molecule may be expressed as a fusion protein, which contains two immunoglobulin-binding domains from Protein G and two immunoglobulin-binding domains from Protein A. In some aspects of this embodiment, one or more of the bacterial immunoglobulin-binding protein domains are modified to, e.g., remove potential sites for glycosylation or other post-translational modifications in eukaryotic cells, improve affinity for certain immunoglobulin isotypes, or improve translation efficiency in mammalian cells by codon optimization.

In another embodiment, the immunoglobulin-capturing molecules consist of single-chain variable fragments (scFv). The scFv is expressed as a fusion protein of the $V_H$ and $V_L$ domains derived from a hybridoma cell line that produces monoclonal antibodies against the heavy chain or light chain constant region of another immunoglobulin molecule (e.g., a common epitope present in all murine IgG isotypes). In some aspects, the scFv capture molecule comprises the $V_H$ domain connected in tandem to the $V_L$ domain by a glycine/serine-rich linker sequence in either order. The glycine/serine-rich linker sequence includes but is not limited to repetitions of (Gly-Gly-Gly-Gly-Ser)$_n$ [as in SEQ ID No. 29] or (Gly-Ser)$_n$ [as in SEQ ID No. 28].

In some embodiments, a polypeptide sequence encoding a transmembrane domain is fused to the immunoglobulin-binding domain in order to tether the immunoglobulin-capturing molecule on the cell surface. Preferably in this embodiment, the transmembrane domain is inert (lacking cell signaling functions) and not prone to internalization. Such a transmembrane domain could be an artificial sequence, or a motif derived from Major Histocompatibility Class I (MHC I), an IgSF molecule such as Lymphocyte-Activation Gene 3 (LAG3 or CD223), or any other transmembrane protein of any species—that is naturally inserted into the plasma membrane upon protein translation.

In other embodiments, the immunoglobulin-capturing molecule contains—in addition to the immunoglobulin-binding domain—a C-terminal peptide sequence for post-translational modification with, e.g., glycosylphosphatidylinositol (GPI), where GPI acts as a tether portion of the immunoglobulin-capturing molecule. GPI is a normal post-translational moiety that comprises a phosphoethanolamine group, a trimannosyl-nonacetylated glucosamine (Man$_3$-GlcN) core, and a phosphatidylinositol group that tethers the protein to the plasma membrane. The phosphoethanolamine group of GPI is linked to a protein C-terminus via a phosphodiester bond. The GPI tether sequences may consist of the C-termini of proteins that are naturally anchored to the ASC plasma membrane by this post-translational process. Table 3 lists exemplary GPI tether or anchor sequences that may be used to construct the immunoglobulin-capturing molecule.

In certain embodiments, the immunoglobulin-capturing molecule contains a "stalk" structure for structural flexibility and support, as well as for increased exposure to the extracellular space. Since the cell surface is ubiquitously crowded with various molecules, the immunoglobulins captured on the immunoglobulin-capturing molecules may be occluded from access to their cognate antigen in the extracellular space by other molecules on the ASC surface. Thus, inclusion of a long stalk in the immunoglobulin-capturing molecule can alleviate any steric hindrance that compromises antigen binding by the displayed immunoglobulins. In preferred aspects of the invention, the stalk of the immunoglobulin-capturing molecule comprises one or more immunoglobulin domains derived from one or more IgSF proteins. Examples of these domains include but are not limited to the immunoglobulin domains of CD2, CD4, or CD22. Additionally, the stalk of the immunoglobulin-capturing molecule may be expressed as a macromolecular complex of two or more subunits. For example, the stalk of the ScFv-containing capture molecule may consist of $C_H2$ and $C_H3$ domains as well as the hinge region of an IgG molecule; thus, the immunoglobulin-capturing molecule is expressed as a homodimer.

Expression of the Immunoglobulin-Capturing Molecule

In certain aspects of the invention, expression of the immunoglobulin-capturing molecules is driven by a promoter derived from a gene that is highly expressed in ASCs but not in immature B cells or antigen-inexperienced mature B cells. These genes include but are not limited to B Lymphocyte-Induced Maturation Protein 1 (Blimp1), Syndecan 1 (Sdc1), Tumor Necrosis Factor Receptor Superfamily Member 17 (Tnfrsf17), and Fucosyltransferase 1 (Fut1). The gene chosen for ASC expression may be of mouse origin, or it may be from another species in which the gene shows an appropriately conserved expression pattern.

In certain other aspects, expression of the immunoglobulin-capturing molecules is driven by an inducible promoter, such as the tetracycline- or tamoxifen-inducible system. The inducible promoter is used to drive the expression of the immunoglobulin-capturing molecule either directly or indirectly via expression of a recombinase such as Cre (see, e.g., Albanese, et al., *Seminars in Cell & Developmental Biology*, 13:129-141 (2002); Sakai, *Methods in Molecular Biology*, 1142:33-40 (2014)). Such inducible expression in ASCs is accomplished either in the transgenic animal or in vitro during culture of ASCs as well as at the stage of hybridoma culture.

In order to express the immunoglobulin-capturing molecule on the cell surface, a signal peptide is included for protein translation in the endoplasmic reticulum. The signal peptide may be a consensus sequence or one that naturally exists as part of cell surface or secreted protein. In preferred aspects of the invention, the signal peptide is derived from that of an immunoglobulin heavy chain [as in SEQ ID Nos. 5-7] or light chain protein [as in SEQ ID Nos 1-3].

In some aspects, in addition to the immunoglobulin-capturing molecule, the expression vector may include an open-reading frame for a reporter protein such as GFP, red fluorescent protein (RFP), or the like. The reporter gene in the expression construct is linked to the immunoglobulin-capturing molecule via, e.g., an IRES sequence or a picornavirus 2A ribosomal skip sequence. Expression of the reporter gene allows for improved purity when used in combination with antigen selection to sort for antigen-specific ASCs.

Transgenes providing for expression of the immunoglobulin-capturing molecules are generated by inserting the coding sequences for the immunoglobulin-capturing molecules into a large piece of genomic DNA containing the gene that is highly expressed in ASCs (e.g, Blimp1 or Tnfrsf17). The insertion can be accomplished by homologous recombination mediated by sequences appended to the ends of the coding fragments, or by other standard molecular biology approaches. The large pieces of genomic DNA may be contained within bacterial artificial chromosome vectors, e.g., such as the pieces of DNA in these vectors that can be obtained from commercially or publicly available genomic DNA libraries.

Transgenic mice (or other animals) expressing the immunoglobulin-capturing molecules may be generated by any facility with the requisite skills using known techniques, as will be understood by one skilled in the art upon reading the present disclosure. Analysis of the animals carrying the transgene is performed using standard methodology such as immunofluorescence microscopy, flow cytometry and/or immunoblotting.

Figure 2A:
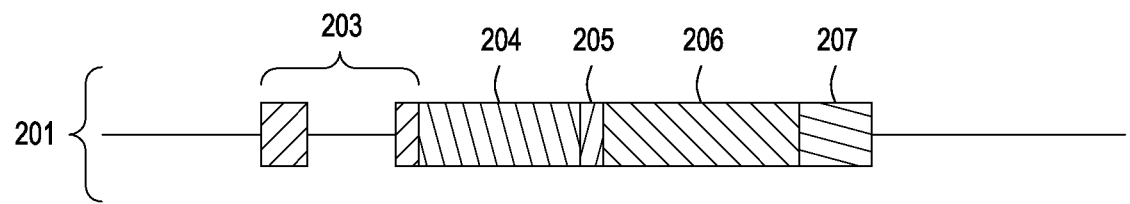
FIG. 2A is a schematic diagram depicting part of a DNA vector encoding an embodiment of an immunoglobulin-capturing molecule.
Figure 2B:
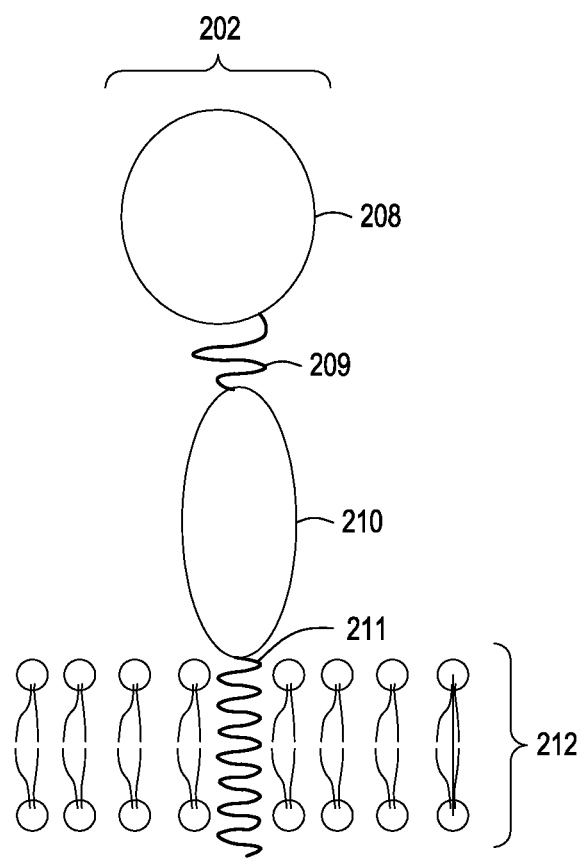
FIG. 2B is a simplified illustration of the embodiment of FIG. 2A expressed as an immunoglobulin-capturing molecule on an ASC surface.

Illustrated in FIGS. 2A and 2B are the transgene (201) and expressed structure (202) of an immunoglobulin-capturing molecule according to one embodiment. The transgene (201) comprises two exons with an intervening intron (203) [SEQ ID Nos. 5-7]. The first exon and the beginning of the second exon encode a leader peptide (e.g., $V_H$ leader peptide). Contiguous with the leader peptide-encoding sequence are sequences encoding the following components: one or more immunoglobulin-binding domains (204) derived from one or more bacterial proteins [e.g., a sequence chosen from SEQ ID Nos. 8-11], a glycine/serine-rich linker (205) [e.g., a sequence chosen from SEQ ID Nos. 12 or 13], a "stalk" structure or region (206) [e.g., a sequence chosen from SEQ ID Nos. 14-16], and a transmembrane domain (207) [e.g., a sequence chosen from SEQ ID No. 17-20]. Following protein translation, the leader peptide is excised from the immunoglobulin-capturing molecule (202), which is expressed as a cell surface protein tethered to the plasma membrane (212). The respective components (208-211) of the immunoglobulin-capturing molecule (202) shown are immunoglobulin-binding domain(s) (208) [e.g., a sequence chosen from SEQ ID Nos. 24-27], glycine/serine-rich linker (209) [e.g., a sequence chosen from SEQ ID Nos. 28 or 29], stalk (210) [e.g., a sequence chosen from SEQ ID Nos. 30-32], and transmembrane domain (211) [e.g., a sequence chosen from SEQ ID Nos. 33-36].

Exemplary nucleic acid sequences for components of the immunoglobulin-capturing molecule illustrated in FIG. 2A (with the expressed structure illustrated in FIG. 2B) are listed in Table 1. The immunoglobulin-capturing molecule may be assembled by combining together one sequence of the several possible options for each component from Table 1 in the order depicted in FIG. 2A (i.e., from N-terminus to C-terminus). For example, a small immunoglobulin-capturing molecule may consist of only two immunoglobulin-binding domains of Protein G, a (glycine-serine)$_3$ linker, and a transmembrane domain without a stalk; while a larger one may contain five Protein A immunoglobulin-binding domains as well as four Protein G immunoglobulin-binding domains, a (Gly-Gly-Gly-Gly-Ser)$_3$ linker, a human CD22 stalk composed of six immunoglobulin folds, and a long human CD7 transmembrane domain.

Figure 3A:
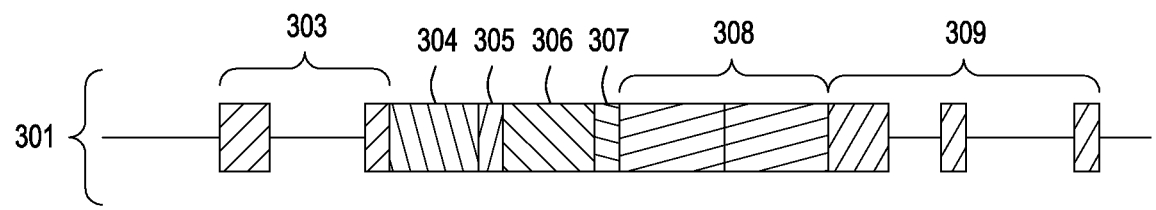
FIG. 3A is a schematic diagram depicting part of a DNA vector encoding an alternative embodiment of an immunoglobulin-capturing molecule.
Figure 3B:
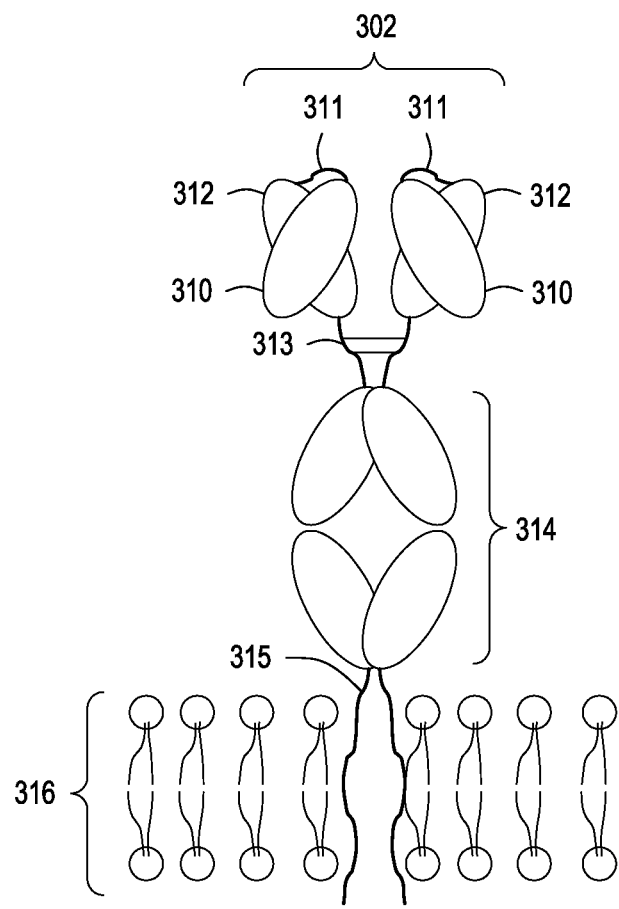
FIG. 3B is a simplified illustration of the embodiment of FIG. 3A expressed as an immunoglobulin-capturing molecule on an ASC surface.

An expression construct and the molecular structure of an alternative embodiment of an immunoglobulin-capturing molecule is illustrated in FIGS. 3A and 3B. In this embodiment of the invention, the transgene (301) similarly comprises a leader sequence encoded by two exons with an intervening intron (303), followed by sequences encoding the components of a scFv with specificity for a part of an immunoglobulin molecule (e.g., a conserved part of the heavy or light chain constant region): $V_H$ (304), glycine/serine-rich linker (305), and $V_L$ (306). For extended protrusion of the immunoglobulin-capturing molecule into the extracellular space, a sequence encoding a stalk comprising a hinge (307) as well as Fc fragment (308) of an immunoglobulin molecule is appended to the scFv-encoding sequence. Finally, one or more exons (309) encoding a transmembrane domain is also included in the expression construct (301). Shown in FIG. 3B is the immunoglobulin-capturing molecule (302) expressed as a homodimer of two subunits, each consisting of a $V_L$ (310) domain, glycine/serine-rich linker (311), and $V_H$ (312) domain of scFv connected to a hinge (313) and Fc (314) of an immunoglobulin molecule. The two subunits of the immunoglobulin-binding portion of the immunoglobulin-capturing molecule are covalently linked via disulfide bonds in the hinge region (313) of each chain. The expressed immunoglobulin-capturing molecule is tethered or anchored into the plasma membrane (316) by a transmembrane domain (315).

Figure 4C:
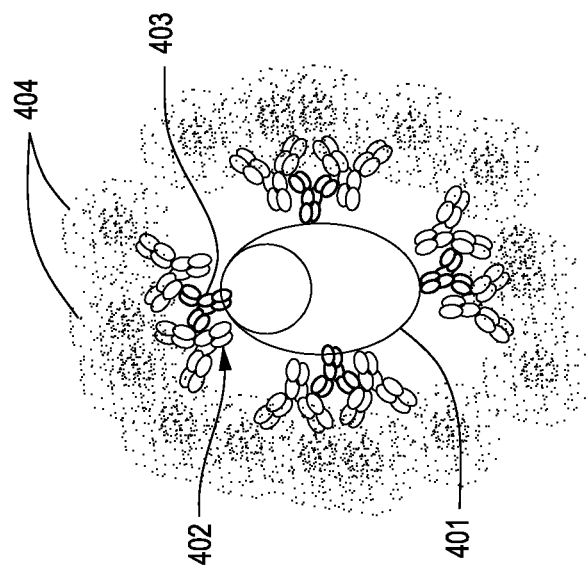
FIGS. 4A, 4B, and 4C are illustrations of a secreting ASC with no immunoglobulin-capturing molecules on the cell surface (FIG. 4A), an ASC with immunoglobulin-capturing molecules and immunoglobulins (i.e., antibodies) on the surface of the ASC (FIG. 4B, also as depicted in detail in FIG. 3B), and labeled antigens bound to the immunoglobulin-capturing molecules expressed on an ASC (FIG. 4C).
Figure 4B:
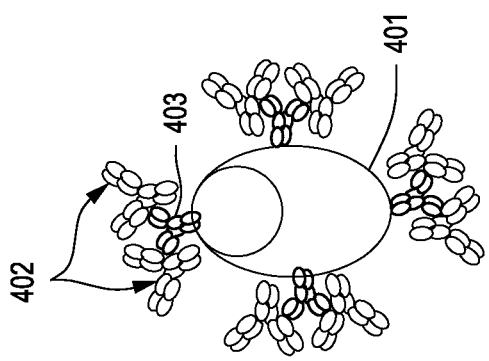
Figure 4A:
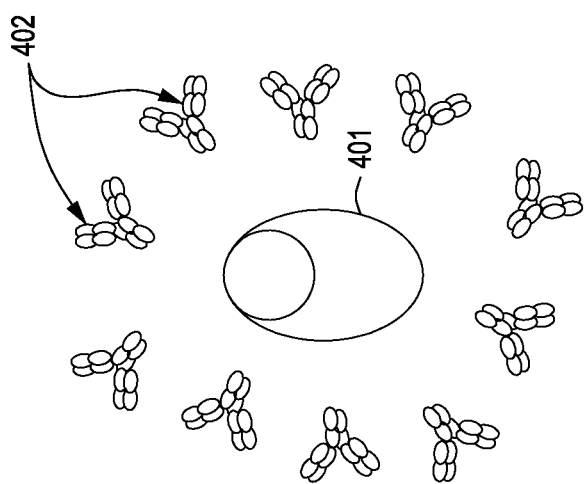

FIG. 4 illustrates the presentation of immunoglobulin-capturing molecules on a cell surface by an scFV embodiment of the immunoglobulin-capturing molecule. As demonstrated previously, an antibody-secreting cell (401) normally does not express the membrane-bound form of antigen receptors and lacks the ability to display on the cell surface the immunoglobulin molecules (402) they secrete. Expression of the scFv version of the immunoglobulin-capturing molecule (403) allows some of the immunoglobulin molecules (402) to be retained on the cell surface as they are being synthesized in the endoplasmic reticulum and subsequently packaged in the vesicles for secretion, or soon after their secretion. Antigen-specific ASCs are then identified by the binding of antigens (404) to the captured immunoglobulin molecules (402) on the cell surface. Detection of antigen binding on the ASCs is accomplished by using antigens that are directly labeled with a fluorophore or any other reporter molecule.

Transgenic Cell Libraries

The transgenic cells of the invention also are used to produce expression libraries, preferably low complexity libraries, for identification of antibodies of interest on the surface of ASCs. The present invention thus also includes antibody libraries produced using the cell technologies of the invention for identification of antigen-specific antibodies expressed on ASCs.

Transgenic Animals

The present invention also provides transgenic animals that have been modified to express immunoglobulin-capturing molecules on the cell surface of ASCs.

In preferred aspects, the transgenic animals of the invention further comprise human immunoglobulin regions.

Numerous methods have been developed for replacing endogenous mouse immunoglobulin regions with human immunoglobulin sequences to create partially- or fully-human antibodies for drug discovery purposes. Examples of such mice include those described in, for example, U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669.

The exons that encode the antibody $V_H$ and $V_L$ domains do not exist in the germ-line DNA. Instead, each $V_H$ or $V_L$ exon is generated, respectively, by the recombination of randomly selected V, D, and J genes present in the H chain locus, or of randomly selected V and J genes in the light chain locus. There are multiple V, D, and J genes in the H chain locus as well as multiple V and J genes in each L chain locus, thus allowing for the generation of a vast antibody diversity repertoire per individual when the permutations of H chain VDJ rearrangements are combined with the permutations of L chain VJ gene rearrangements.

In particularly preferred aspects, the transgenic animals of the invention are as described in co-pending application US Pub. No. 2013/0219535, which is incorporated by reference in its entirety herein. Such transgenic animals have a genome comprising an introduced partially human immunoglobulin region, wherein the endogenous non-human V, D, and J gene coding sequences have been replaced with those of human origin without altering the endogenous noncoding sequences. Preferably, the transgenic cells and animals of the invention have genomes in which part or all of the endogenous immunoglobulin genes are removed.

In other aspects, the transgenic animals of the invention are avian, preferably chickens.

Use in Antibody Production

Culturing cells in vitro has been the basis of the production of numerous therapeutic biotechnology products, and involves the production of protein products in cells and release into the support medium. The quantity and quality of protein production over time from the cells growing in culture depends on a number of factors, such as, for example, cell density, cell cycle phase, cellular biosynthesis rates of the proteins, condition of the medium used to support cell viability and growth, and the longevity of the cells in culture. (See, for example, Fresney, *Culture of Animal Cells*, Wiley, Blackwell (2010); and *Cell Culture Technology for Pharmaceutical and Cell-Based Therapies*, Ozturk and Ha, Eds., CRC Press, (2006).)

For certain products, such as monoclonal antibodies, enhancing the presence and protein-expression efficiency of the cells that are actually producing the product is a key aspect of efficient protein production. Capturing antibodies on the surface of ASCs secreting them provides opportunities for discriminating ASCs on the basis of their immunoglobulin specificities, and this in turn provides opportunities for optimizing and enhancing the production of antibodies for various uses.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to terms and numbers used (e.g., vectors, amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Figure 5A:
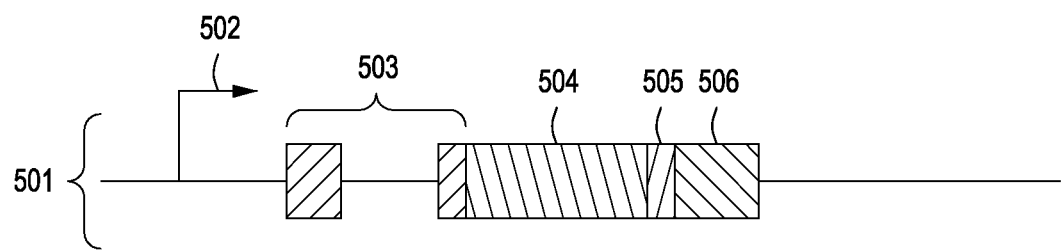
FIG. 5A is a schematic diagram depicting part of a DNA vector encoding an exemplary embodiment of an immunoglobulin-capturing molecule.

Example 1: Expression of a Minimal Protein G-Containing Membrane-Bound Immunoglobulin-Capturing Molecule An expression vector encoding a small membrane-bound form of the immunoglobulin-capturing molecule without a stalk is generated by direct DNA synthesis or standard molecular cloning techniques. A diagram of the protein-coding part of this vector (501) is shown in FIG. 5A. The expression vector encodes two immunoglobulin-binding domains of streptococcal Protein G (504) [SEQ ID No. 8] that are tethered to the cell surface by means of a membrane-spanning domain derived the human LAGS (or CD223) protein (506) [SEQ ID No. 17]. A fragment of DNA encoding a short linker consisting of Gly-Ser-Gly-Ser-Gly-Ser sequence (505) [SEQ ID No. 28] is placed between the DNA fragments encoding the Protein G immunoglobulin-binding domains (504) and the transmembrane domain (506) to provide structural flexibility to the expressed protein. Finally, a sequence encoding a signal peptide (leader peptide) (503) is included in the construct to allow for extrusion of the immunoglobulin-capturing molecule into the lumen of the endoplasmic reticulum during its biosynthesis. The signal peptide sequence in this example is derived from an immunoglobulin light chain variable ($V_L$) gene segment which includes its native intron (503) [SEQ ID Nos. 1-3]. The promoter is indicated at (502). The nucleotide and amino acid sequences of various components comprising the immunoglobulin-capturing molecule in this example are specified in Table 1 and Table 2, respectively.

The expression vector is transfected into various myeloma, hybridoma or other cell lines using commonly accessible methodology such as electroporation. The transfected cells are then examined for surface expression of the immunoglobulin-capturing molecule using procedures such as immunofluorescence microscopy, flow cytometry, and/or immunoblotting of the membrane protein fractions. The cells are further analyzed using a subset of these procedures for the capacity of the cell surface immunoglobulin-capturing molecules to retain immunoglobulins produced by the transfected cells or added to them.

Figure 5B:
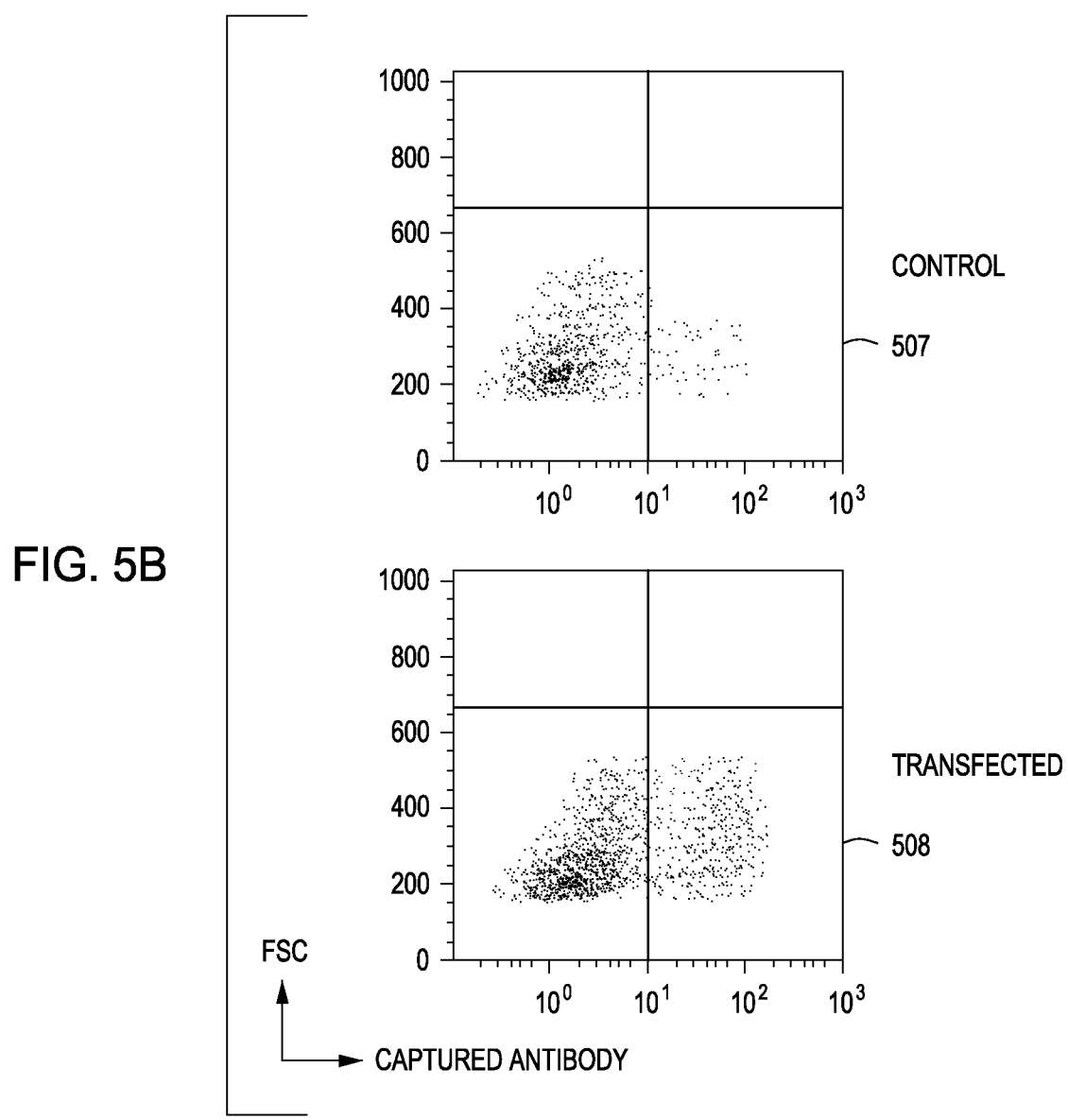
FIG. 5B provides two flow cytometry scatter plots showing the results of retention of secreted immunoglobulin molecules on the cell surface of transfected RPMI 8226 (ATCC® CCL-155™) human cells per the methods of the invention.

FIG. 5B illustrates the expression of this small immunoglobulin-capturing molecule in a plasmacytoma cell line and its ability to retain immunoglobulin molecules on the cell surface. Human RPMI 8226 (ATCC® CCL-155™) cells were transfected with DNA plasmids encoding the immunoglobulin-capturing molecule (501) under control of the Blimp1 promoter (502). The cells were also co-transfected with a plasmid encoding mouse IgG. Compared to untransfected cells (top, 507), the transfected cells (bottom, 508) exhibit captured immunoglobulins on the cell surface.

Transgenic animals are then generated to express the membrane-bound immunoglobulin-capturing molecules containing Protein G on the ASCs, and the capacity of the transgene-encoded molecules to capture immunoglobulins on ASCs is determined directly on the ASCs taken from the transgenic mice by standard flow cytometry.

Example 2: Expression of a Protein G-Containing Membrane-Bound Immunoglobulin-Capturing Molecule Containing a Stalk An expression vector encoding a membrane-bound form of the immunoglobulin-capturing molecule containing a long stalk is generated by direct DNA synthesis or standard molecular cloning techniques. The expression vector encodes three immunoglobulin-binding domains derived from the C-terminal half of streptococcal Protein G [SEQ ID No. 9]. DNA fragments encoding a short linker consisting of Gly-Ser-Gly-Ser-Gly-Ser [SEQ ID No. 28] sequence, a stalk consisting of six immunoglobulin domains derived from human CD22 protein [SEQ ID No. 16], and a transmembrane domain derived from human CD58 [SEQ ID No. 18] are appended to the immunoglobulin-binding domain-encoding DNA fragment of the vector. Finally, a sequence encoding a signal peptide (leader peptide) is placed preceding the entire open-reading frame of the immunoglobulin-capturing molecule to allow for extrusion of the translated protein into the lumen of the endoplasmic reticulum during its biosynthesis. The sequences encoding the signal peptide in this example are derived from an immunoglobulin heavy chain variable ($V_H$) gene segment and include its native intron [SEQ ID Nos. 5-7]. The nucleotide and amino acid sequences of components comprising the immunoglobulin-capturing molecule in this example are specified in Table 1 and Table 2, respectively.

The expression vector is transfected into various myeloma, hybridoma or other cell lines using commonly accessible methodology such as electroporation. The transfected cells are then examined for surface expression of the Protein G molecule using procedures such as immunofluorescence microscopy, flow cytometry and immunoblotting of the cell membrane protein fractions. The cells are further analyzed using a subset of these procedures for the capacity of the cell surface Protein G to capture immunoglobulins produced by the transfected cells or added to them.

Transgenic animals are then generated to express the membrane-bound immunoglobulin-capturing molecules consisting of Protein G, CD22 and CD58 fusion in the ASCs, and the capacity of the transgene-encoded molecules to capture immunoglobulins on ASCs is determined directly on the ASCs taken from the transgenic mice by standard flow cytometry.

Example 3: Expression of a Protein G-Containing Immunoglobulin-Capturing Molecule Anchored to the Membrane by a GPI Post-Translational Modification An expression vector encoding two immunoglobulin-binding domains derived from the streptococcal Protein G is synthesized. Included in this expression vector downstream of the Protein G-encoding sequence are DNA fragments that encode the following: a Gly/Ser-rich linker sequence, a stalk consisting of two immunoglobulin domains of human CD4, and a GPI anchor sequence. Finally, a signal peptide sequence (leader sequence) is included in the construct to allow for extrusion of the translated protein into the lumen of the endoplasmic reticulum during its biosynthesis. The sequences encoding the signal peptide in this example are derived from an immunoglobulin light chain variable ($V_L$) gene segment and include its native intron. The nucleotide and amino acid sequences of components comprising the immunoglobulin-capturing molecule in this example are specified in Table 1 and Table 2, respectively. The GPI anchor sequences are specified in Table 3.

The expression vector is transfected into various myeloma, hybridoma or other cell lines using commonly accessible methodology such as electroporation. The transfected cells are then examined for surface expression of the Protein G molecule using procedures such as immunofluorescence microscopy, flow cytometry and immunoblotting of the cell membrane protein fractions. The cells are further analyzed using a subset of these procedures for the capacity of the cell surface Protein G to capture immunoglobulins produced by the transfected cells or added to them.

Transgenic animals are then generated to express the GPI-anchored immunoglobulin-capturing molecules in ASCs, and the capacity of the transgene-encoded molecules to capture immunoglobulins on the surface of ASCs is determined directly on the ASCs taken from the transgenic mice by standard flow cytometry.

Example 4: Expression of a Membrane-Bound scFv Derived from an Antibody Specific for an Immunoglobulin Constant Region An expression vector encoding a scFv specific for the constant domain of an immunoglobulin is generated by standard molecular cloning or direct DNA synthesis. In this example, the single-chain antibody is specific for the constant domain of the mouse kappa light chain, which is present in more than 90% of antibodies found in normal mice. The exon encoding the scFv comprises $V_L$, linker, and $V_H$ sequences specified at [SEQ ID Nos. 43-48, respectively]. Included in this expression vector downstream of the ScFv-encoding sequence is a contiguous sequence that encodes the Fc part of rat IgG1 consisting of the following: a hinge region, $C_H2$ domain, and $C_H3$ domain of the secreted form. The rat IgG1 Fc-encoding sequence is specified at [SEQ ID Nos. 49]. The vector also includes sequences encoding the transmembrane domain of a mouse Major Histocompatibility Complex Class I protein (the mouse K molecule from the b haplotype), specified at [SEQ ID Nos. 50-54].

The expression vector is transfected into various myeloma, hybridoma and other cell lines using commonly accessible methodology such as electroporation. The transfected cells are examined for surface expression of the single chain antibody molecule using procedures such as immunofluorescence microscopy, flow cytometry and immunoblotting of the cell membrane protein fractions. The cells are further analyzed using a subset of these procedures for the capacity of the cell surface single chain antibody molecule to capture immunoglobulins produced by the transfected cells or added to them.

Transgenic animals are generated to express the scFv-containing immunoglobulin-capturing molecules on ASCs, and the capacity of the transgene-encoded molecules to capture immunoglobulins on the surface of ASCs is determined by standard flow cytometry directly on the ASCs taken from the mice.

Example 5: Use of Transgenic Animal Expressing Immunoglobulin-Capturing Molecules to Isolate ASCs Producing Monoclonal Antibodies Against Antigen of Interest Transgenic mice are generated using a bacterial artificial chromosome vector containing the promoter of human TNFRSF17 gene, the coding sequence of an immunoglobulin-capturing molecule, for example as in Examples 1-4, an IRES sequence, and GFP. Spleen, lymph nodes, and bone marrow from several transgenic founder lines are harvested, processed, and analyzed for the expression of GFP as well as the immunoglobulin-capturing molecule by standard flow cytometry. GFP-positive cells from the transgenic mice are then pooled, sorted, and verified by enzyme-linked immunospot (ELISPOT) for their ability to secrete immunoglobulins. A transgenic line that stably expresses detectable levels of GFP and the immunoglobulin-capturing molecule is selected for propagation.

Adult transgenic mice are immunized with an antigen of interest. Spleens as well as the relevant lymph nodes are isolated from the immunized mice, processed, and stained for flow cytometric analyses. Additionally, the isolated cells are subjected to antigen binding during the flow cytometric staining. The antigen is either directly labeled with a fluorophore or with biotin for use with a labeled avidin, streptavidin, or similar system. ASCs are sorted on the basis of GFP-positive staining as well as antigen-positive staining.

The purified ASCs are then fused to myeloma cells to generate hybridoma cells using established methodologies familiar to those with ordinary skill in the art. In this invention, the provided methods to express the immunoglobulin-capturing molecules also allow for the screening of hybridoma cells based on GFP expression as well as positive staining of antigens captured on the cell surfaces.

Alternatively, the purified ASCs are individually sorted, and genes encoding their $V_H$ and $V_L$ domains are cloned via RT-PCR or 5' RACE techniques adapted for single cells. The cloned $V_H$- and $V_L$-coding sequences are subcloned into an expression vector containing a sequence encoding the desired constant regions of heavy chain and light chain, respectively. The $V_H$- and $V_L$-expression vectors are transfected into a HEK-293T or CHO cell lines, and the secreted monoclonal antibodies are further tested for antigen binding and other functions.

TABLE 1 exemplary nucleic acid sequences

| SEQ ID No. | Description | Corresponding Structure | Sequence |
|---|---|---|---|
| 1 | Leader Exon1/ Intron/ Exon 2/ Tags $V_L$ Leader Exon 1 | FIG. 2A, 203 FIG. 3A, 303 FIG. 5A, 503 | ATGGACATCAGGGCTCCTGCTCAGTTTCTTG GCATCTTGTTGCTCTGGTTTCCAG |
| 2 | Leader Exon1/ Intron/ Exon 2/ Tags $V_L$ intron | FIG. 2A, 203 FIG. 3A, 303 FIG. 5A, 503 | GTAAAATGAACTAAAATGGGAATTTCACTGT AAGTGTTGACAGGCATTTGGGGACTGTGTTC TTTTTATCATGCTTACCTTTGTAGATATTCAT TATGTCTCCACTCCTAG |
| 3 | Leader Exon1/ Intron/ Exon 2/ Tags $V_L$ Leader Exon 2 | FIG. 2A, 203 FIG. 3A, 303 FIG. 5A, 503 | GTGCCAGATGTGACATCCAGATG |
| 4 | Leader Exon1/ Intron/ Exon 2/ Tags FLAG + Myc Tags | FIG. 2A, 203 FIG. 3A, 303 FIG. 5A, 503 | GACTACAAGGATGACGACGACAAGGGCAGC GGCGAACAGAAGCTGATTTCGGAGGAGGAC CTG |
| 5 | Leader Exon1/ Intron/ Exon 2/ Tags $V_H$ Leader Exon 1 | FIG. 2A, 203 FIG. 3A, 303 FIG. 5A, 503 | ATGGGATGGAGCTGTATCATGCTCTTCTTGG CAGCAACAGCTACAG |
| 6 | Leader Exon1/ Intron/ Exon 2/ Tags $V_H$ Intron | FIG. 2A, 203 FIG. 3A, 303 FIG. 5A, 503 | GTAAGGGGCTCACAGTAGCAGGCTTGAGGTC TGGACATATACATGGGTGACAATGACATCCA CTTTGCCTTTCTCTCCACAG |
| 7 | Leader Exon1/ Intron/ Exon 2/ Tags $V_H$ | FIG. 2A, 203 FIG. 3A, 303 FIG. 5A, 503 | GTGTCCACTCCCAGGTCCAACTG |
| 8 | Ig-Binding Domain 2-Domain Protein G | FIG. 2A, 204 FIG. 5A, 504 | GGTACCCCAGCCGTGACCACCTACAAGCTCG TCATCAACGGAAAGACGCTCAAGGGCGAAA CCACTACCAAGGCGGTGGATGCCGAAACCGC CGAAAAGGCCTTCAAGCAGTACGCTAACGAC AATGGGGTGGACGGAGTCTGGACGTACGAT GATGCCACCAAGACTTTCACCGTGACCGAAG TGAACACTCCGGCCGTCACCACTTATAAGCT CGTGATCAACGGGAAAACCCTGAAGGGAGA GACTACCACAAAGGCCGTGGATGCTGAGACT GCAGAGAAGGCGTTCAAACAGTACGCCAAC GACAACGGCGTGGACGGCGTCTGGACCTACG ATGACGCCACTAAGACCTTCACTGTGACCGA A |
| 9 | Ig-Binding Domain 3-Domain Protein G | FIG. 2A, 204 FIG. 5A, 504 | ATAGATGAAATTTTAGCTGCATTACCTAAGA CTGACACTTACAAATTAATCCTTAATGGTAA AACATTGAAAGGCGAAACAACTACTGAAGC TGTTGATGCTGCTACTGCAGAAAAAGTCTTC AAACAATACGCTAACGACAACGGTGTTGACG GTGAATGGACTTACGACGATGCGACTAAGAC CTTTACAGTTACTGAAAAACCAGAAGTGATC GATGCGTCTGAATTAACACCAGCCGTGACAA CTTACAAACTTGTTATTAATGGTAAAACATT GAAAGGCGAAACAACTACTGAAGCTGTTGAT GCTGCTACTGCAGAAAAAGTCTTCAAACAAT ACGCTAACGACAACGGTGTTGACGGTGAATG GACTTACGACGATGCGACTAAGACCTTTACA GTTACTGAAAAACCAGAAGTGATCGATGCGT CTGAATTAACACCAGCCGTGACAACTTACAA ACTTGTTATTAATGGTAAAACATTGAAAGGC GAAACAACTACTAAAGCAGTAGACGCAGAA ACTGCAGAAAAAGCCTTCAAACAATACGCTA ACGACAACGGTGTTGATGGTGTTTGGACTTA TGATGATGCGACTAAGACCTTTACGGTAACT GAA |

TABLE 1-continued exemplary nucleic acid sequences

| SEQ ID No. | Description | Corresponding Structure | Sequence |
|---|---|---|---|
| 10 | Ig-Binding Domain 2-Domain Protein A + 2-Domain Protein G | FIG. 2A, 204 FIG. 5A, 504 | GTGGATAACAAGTTCAACAAGGAACAGCAGAACGCCTTTTACGAGATTCTGCATCTGCCCAACCTGAATGAGGAACAGCGGAACGCATTCATTCAGTCTCTGAAGGATGATCCTAGCCAGTCGGCCAACCTCCTGGCTGAAGCAAAGAAGCTGAACGATGCCCAAGCGCCCAAAGTGGACAACAAGTTTAACAAGGAGCAGCAGAATGCTTTCTACGAGATCCTGCACCTCCCGAATCTGAACGAGGAGCAGAGAAACGCCTTCATCCAATCACTGAAGGACGACCCGTCACAGTCCGCCAACCTTCTGGCGGAAGCCAAGAAACTGAACGACGCCCAGGCGCCAAAGGTGGACGGATCCGGGTCCGGCAGCGGTACCCCAGCCGTGACCACCTACAAGCTCGTCATCAACGGAAAGACGCTCAAGGGCGAAACCACTACCAAGGCGGTGGATGCCGAAACCGCCGAAAAGGCCTTCAAGCAGTACGCTAACGACAATGGGGTGGACGGAGTCTGGACGTACGATGATGCCACCAAGACTTTCACCGTGACCGAAGTGAACACTCCGGCCGTCACCACTTATAAGCTCGTGATCAACGGGAAAACCCTGAAGGGAGAGACTACCACAAAGGCCGTGGATGCTGAGACTGCAGAGAAGGCCGTTCAAACAGTACGCCAACGACAACGGCGTGGACGGCGTCTGGACCTACGATGACGCCACTAAGACCTTCACTGTGACCGAA |
| 11 | Ig-Binding Domain 5-Domain Protein A + 4-Domain Protein G | FIG. 2A, 204 FIG. 5A, 504 | GCCAATGCCGCCCAGCACGACGAGGCTCAGCAGAACGCATTCTACCAGGTGCTGAACATGCCAAACCTCAACGCCGATCAGCGCAATGGTTTCATTCAGTCCCTGAAGGACGATCCGAGCCAGTCAGCTAACGTGCTCGGGGAGGCCCAAAAGCTGAATGACTCCCAGGCGCCGAAGGCCGACGCCCAGCAAAACAACTTCAACAAGGATCAGCAATCCGCCTTCTATGAAATCCTGAATATGCCTAACCTGAACGAAGCTCAGCGAAATGGGTTCATCCAGAGCCTTAAGGACGACCCTAGCCAGTCCACCAACGTGCTGGGGGAGGCCAAGAAACTTAACGAATCCCAGGCCCCGAAGGCGGACAACAACTTTAACAAGGAACAGCAAAATGCGCCCAACGTTTCATCCAGTCCCTGAAGGACGATCCATCCCAGTCCGCCAACCTGTTGAGCGAGGCGAAGAAGCTGAATGAGTCCCAAGCCCCCAAGGCTGACAACAAGTTCAATAAGGAACAACAGAATGCCTTCTACGAAATTCTGCACTTGCCCAATCTGAACGAGGAGCAGCGCAACGGCTTCATCCAATCTCTGAAAGACGACCCGTCGCAGTCGGCCAACTTGCTGGCCGAAGCCAAGAAGCTCAACGACGCTCAGGCCCCTAAGGCCGACAACAAGTTCAACAAAGAGCAACAGAACGCGTTCTACGAGATTCTCCACTTGCCGAACCTGACCGAAGAACAACGGAACGGATTCATTCAGAGCCTGAAGGATGACCCTTCGGTGTCAAAGGAGATCCTGGCAGAAGCCAAAAAGCTGAACGATGCCCAGGCACCAAAGGAAGAGGACAACAACAAGCCGGGCGACCCGAGGGATCTCCGAAGCCACTGATGGGCTGTCCGATTTTCTGAAGTCACAGACTCCTGCTGAGGACACCGTGAAGTCCATCGAGCTCGCCGAGGCCAAGGTGCTGGCCAACCGGGAGCTGGACAAGTACGGAGTGTCCGACTACTACAAAAACCTGATTAACAACGCCAAGACTGTGGAAGGAGTGAAGGCATTGATCGATGAAATCCTGGCGGCGCTCCCAAAACCGACACCTACAAACTGATTCTCAACGGAAAGACGCTGAAGGGGGAAACTACCACCGAAGCGGTGGACGCCGCCACCGCCGAAAAGGTGTTTAAGCAGTATGCTAACGACAACGGTGTCGACGGAGAGTGGACTTACGACGACGCCACTAAGACTTTCACCGTGACCGAGAAGCCCGAGGTCATCGACGCGAGCGAGCTCACTCCCGCCGTGACCACCTACAAGCTGGTCATCAATGGAAAGACTCTGAAGGGCGAAACTACTACTGAAGCCGTGGATGCGGCAACCGCCGAGAAAGTGTTCAAGC |
| 12 | Gly/Ser Linker | FIG. 2A, 205 FIG. 3A, 305 FIG. 5A, 505 | GGATCCGGCTCCGGATCC |
| 13 | Gly/Ser Linker | FIG. 2A, 205 FIG. 3A, 305 FIG. 5A, 505 | GGAGGCGGAGGCAGCGGAGGCGGTGGCTCGGGAGGCGGAGGCTCG |
| 14 | Stalk Rat CD2 | FIG. 2A, 206 FIG. 5A, 506 | GAGATGGTGTCCAAGCCGATGATCTACTGGGAGTGTTCCAACGCGACTCTGACCTGTGAAGTGCTGGAGGGAACCGACGTGGAACTGAAGCTGTACCAGGGTAAAGAACATCTGCGGTCGTTGCGCCAAAAGACCATGAGCTACCAGTGGACCAACTTGCGGGCGCCTTTCAAGTGCAAAGCCGTCAATAGAGTGTCCAGGAGAGCGAAATGGAGGTCGTGAACTGCCCCGAAAAGGGACTG |
| 15 | Stalk Rat CD4 | FIG. 2A, 206 FIG. 5A, 506 | TCAACTTCCATCACCGCCTACAAGAGCGAGGGAGAGAGCGCCGAGTTTTCCTTCCCCCTGAACCTGGGCGAAGAAAGCCTCCAGGGAGAACTGCGCTGGAAGGCAGAAAAGGCCCCAAGCTCTCAGTCCTGGATCACCTTCAGCCTGAAGAACCAGAAGGTGTCCGTGCAGAAGTCCACTTCAAACCCGAAGTTCCAGCTCTCCGAAACCCTCCCTCTGACCCTGCAAATCCCTCAAGTGTCGCTGCAATTCGCGGGGAGCGGAAATCTGACTCTGACTCTTGACCGGGCATCTTGTACCAGGAGGTGAACCTGGTGGTCATGAAGGTGACCCAGCCCGATAGCAACACCCTGACCTGTGAAGTGATGGGACCCACGTCCCCGAAGATCGGCTCATTCTGAAGCAGGAGAACCAGGAGGCTCGGGTGTCCAGACAGGAAAGGTCATCCAAGTGCAGGCCCCCGGAAGCCGGCGTGTGGCAGTGCCTGCTGTCCGAGGGAGAGGAAGTCAAGATGGACTCGAAAATCCAGGTGCTGTCCAAAGGGCTGAACCAGACTATG |
| 16 | Stalk Human CD22 | FIG. 2A, 206 FIG. 5A, 506 | GAAAGGCCTTTTCCACCTCATATCCAGCTCCCTCCAGAAATTCAAGAGTCCCAGGAAGTCACTCTGACCTGCTTGCTGAATTTCTCCTGCTATGGGTATCCGATCCAATTGCAGTGGCTCCTAGAGGGGGGTTCCAATGAGGCAGGCTGCTGTCACCTCGACCTCCTTGACCATCAAGTCTGTCTTCACCCGGAGCGAGCTCAAGTTCTCCCCACAGTGGAGTCACCATGGGAAGATTGTGACCTGCCAGCTTCAGGATGCAGATGGGAAGTTCCTCTCCAATGACACGGTGCAGCTGAACGTGAAGCACACCCCGAAGTTGGAGATCAAGGTCACTCCCAGTGATGCCATAGTGAGGGAGGGGGACTCTGTGACCATGACCTGCGAGGTCAGCAGCAGCAACCCGGAGTACACGACGGTATCCTGGCTCAAGGATGGGACCTGCTGAAGAAGCAGAATACATTCACGCTAAACCTGCGCGAAGTGACCAAGGACCAGAGTGGGAAGTACTGCTGTCAGGTCTCCAATGACGTGGGCCCGGGAAGGTCGGAAGAAGTGTTCCTGCAAGTGCAGTATGCCCCGGAACCTT |

TABLE 1-continued exemplary nucleic acid sequences

| SEQ ID No. | Description | Corresponding Structure | Sequence |
|---|---|---|---|
| | | | CCACGGTTCAGATCCTCCACTCACCGGCTGT GGAGGGAAGTCAAGTCGAGTTTCTTTGCATG TCACTGGCCAATCCTCTTCCAACAAATTACA CGTGGTACCACAATGGGAAAGAAATGCAGG GAAGGACAGAGGAGAAAGTCCACATCCCAA AGATCCTCCCCTGGCACGCTGGGACTTATTC CTGTGTGGCAGAAAACATTCTTGGTACTGGA CAGAGGGGCCCGGGAGCTGAGCTGGATGTC CAGTATCCTCCCAAGAAGGTGACCACAGTGA TTCAAAACCCCATGCCGATTCGAGAAGGAGA CACAGTGACCCTTTCCTGTAACTACAATTCC AGTAACCCCAGTGTTACCCGGTATGAATGGA AACCCCATGGCGCCTGGAGGAGCCATCGCT TGGGGTGCTGAAGATCCAAAACGTTGGCTGG GACAACACAACCATCGCCTGCGCAGCTTGTA ATAGTTGGTGCTCGTGGGCCTCCCCTGTCGC CCTGAATGTCCAGTATGCCCCCCGAGACGTG AGGGTCCGGAAAATCAAGCCCCTTTCCGAGA TTCACTCTGGAAACTCGTCAGCCTCCAATG TGACTTCTCAAGCAGCCACCCCAAAGAAGTC CAGTTCTTCTGGGAGAAAAATGGCAGGCTTC TGGGGAAAGAAAGCCAGCTGAATTTTGACTC CATCTCCCCAGAAGATGCTGGGAGTTACAGC TGCTGGGTGAACAACTCCATAGGACAGAGC CGTCAAGGCCTGGACACTTGAAGTGCTGTA TGCACCCAGGAGGCTGCGTGTGTCCATGAGC CCGGGGGACCAAGTGATGGAGGGGAAGAGT GCAACCCTGACCTGTGAGAGCGACGCCAACC CTCCCGTCTCCCACTACACCTGGTTTGACTG GAATAACCAAAGCCTCCCCTACCACAGCCAG AAGCTGAGATTGGAGCCGGTGAAGGTCCAG ACTCGGGTGCCTACTGGTGCCAGGGGACCAA CAGTGTGGGCAAGGGCCGTTCGCCTCTCAGC ACCCTCACCGTCTACTATAGCCCGGAGACC |
| 17 | Transmembrane Domain Human LAG3 | FIG. 2A, 207 FIG. 5A, 507 | GCGCCTGGAGCGCTGCCGGCCGGTCATCTGT TGTTGTTCCTGACCCTGGGGGTGCTGTCACT GCTGCTGCTCGTGACCGGGGCATTCGGTTTC CACCTGTGGAGAAGGCAGTGGCGGTAG |
| 18 | Transmembrane Domain Human CD58 | FIG. 2A, 207 FIG. 5A, 507 | CATTCCCGGCACCGCTACGCGCTGATTCCGA TTCCTCTGGCCGTGATCACCACCTGTATCGT GCTCTACATGAACGGTATCCTGAAATGCGAC AGAAAGCCCGACAGGACTAACAGCAATTAG |
| 19 | Transmembrane Domain Rat CD2 | FIG. 2A, 207 FIG. 5A, 507 | CCGCTGTACCTGATCGTGGGGGTGTCAGCCG GCGGTCTGCTGCTCGTGTTCTTCGGGGCACT GTTCATCTTCTGCATTTGCAAGAGGAAGAAG CGGTAG |
| 20 | Transmembrane Domain Human CD7 | FIG. 2A, 207 FIG. 5A, 507 | CCACCCCGGGCGTCCGCACTGCCGGCGCCCC CTACCGGAAGCGCGCTGCCCGATCCGCAAAC CGCCAGCCCTGCCTGCCGCACTGGCCGTGGCT CATTCCTGCTGGGTCTGGGCTCGGGGTGGC CGCGTGTTGGCACGGACTCAGATCAAGAAG CTGTGCTCCTGGAGAGACAAAAACTCCGCCG CCTGTGTGGTGTACGAGGACATGTCACACTC GAGGTGCAATACCCTGTCCTCGCCGAACCAG TACCAGTAG |

TABLE 2 exemplary peptide sequences

| SEQ ID No. | Description | Corresponding Structure | Sequence |
|---|---|---|---|
| 21 | Leader Exon1/ Intron/ Exon 2/Tags $V_L$ Leader Exon | | MGWSCIMLFLAATATGVHSQVQL |
| 22 | Leader Exon1/ Intron/ Exon 2/Tags FLAG + Myc Tags | | DYKDDDDKGSGEQKLISEEDL |
| 23 | Leader Exon1/ Intron/ Exon 2/Tags $V_H$ Leader Exon | | MDIRAPAQFLGILLLWFPGARCDIQM |
| 24 | Ig-Binding Domain 2-Domain Protein G | FIG. 2B, 208 | GTPAVTTYKLVINGKTLKGETTTKAVDAET AEKAFKQYANDNGVDGVWTYDDATKTFTVT EVNTPAVTTYKLVINGKTLKGETTTKAVDA ETAEKAFKQYANDNGVDGVWTYDDATKTFT VTE |
| 25 | Ig-Binding Domain 3-Domain Protein G | FIG. 2B, 208 | IDEILAALPKTDTYKLILNGKTLKGETTTE AVDAATAEKVFKQYANDNGVDGEWTYDDAT KTFTVTEKPEVIDASELTPAVTTYKLVING KTLKGETTTEAVDAATAEKVFKQYANDNGV DGEWTYDDATKTFTVTEKPEVIDASELTPA VTTYKLVINGKTLKGETTTKAVDAETAEKA FKQYANDNGVDGVWTYDDATKTFTVTE |
| 26 | Ig-Binding Domain 2-Domain Protein A + 2-Domain Protein G | FIG. 2B, 208 | VDNKFNKEQQNAFYEILHLPNLNEEQRNAF IQSLKDDPSQSANLLAEAKKLNDAQAPKVD NKFNKEQQNAFYEILHLPNLNEEQRNAFIQ SLKDDPSQSANLLAEAKKLNDAQAPKVDGS GSGSGTPAVTTYKLVINGKTLKGETTTKAV DAETAEKAFKQYANDNGVDGVWTYDDATKT FTVTEVNTPAVTTYKLVINGKTLKGETTTK AVDAETAEKAFKQYANDNGVDGVWTYDDAT KTFTVTE |
| 27 | Ig-Binding Domain 5-Domain Protein A + 4- | FIG. 2B, 208 | ANAAQHDEAQQNAFYQVLNMPNLNADQRNG FIQSLKDDPSQSANVLGEAQKLNDSQAPKA DAQQNNFNKDQQSAFYEILNMPNLNEAQRN GFIQSLKDDPSQSTNVLGEAKKLNESQAPK ADNNFKEQQNAFYEILNMPNLNEEQRNGFI QSLKDDPSQSANLLSEAKKLNESQAPKAD NKFNKEQQNAFYEILHLPNLNEEQRNGFIQ SLKDDPSQSANLLAEAKKLNDAQAPKADNK FNKEQQNAFYEILHLPNLTEEQRNGFIQSL |

TABLE 2-continued exemplary peptide sequences

| SEQ ID No. | Description | Corresponding Structure | Sequence |
|---|---|---|---|
| | Domain Protein G | | KDDPSVSKEILAEAKKLNDAQAPKEEDNNK PGDPRISEATDGLSDFLKSQTPAEDTVKSI ELAEAKVLANRELDKYGVSDYYKNLINNAK TVEGVKALIDEILAALPKTDTYKLILNGKT LKGETTTEAVDAATAEKVFKQYANDNGVDG EWTYDDATKTFTVTEKPEVIDASELTPAVT TYKLVINGKTLKGETTTEAVDAATAEKVFK QYANDNGVDGEWTYDDATKTFTVTEKPEVI DASELTPAVTTYKLVINGKTLKGETTTKAV DAETAEKAFKQYANDNGVDGVWTYDDATKT FTVTEMVTEVP |
| 28 | Gly/Ser Linker | FIG. 2B, 209 | GSGSGS |
| 29 | Gly/Ser Linker | FIG. 2B, 209 | GGGGSGGGGSGGGGS |
| 30 | Stalk Rat CD2 | FIG. 2B, 210 | EMVSKPMIYWECSNATLTCEVLEGTDVELK LYQGKEHLRSLRQKTMSYQWTNLRAPFKCK AVNRVSQESEMEVVNCPEKGL |
| 31 | Stalk Rat CD4 | FIG. 2B, 210 | STSITAYKSEGESAEFSFPLNLGEESLQGE LRWKAEKAPSSQSWITFSLKNQKVSVQKST SNPKFQLSETLPLTLQIPQVSLQFAGSGNL TLTLDRGILYQEVNLVVMKVTQPDSNTLTC EVMGPTSPKMRLILKQENQEARVSRQEKVI QVQAPEAGVWQCLLSEGEEVKMDSKIQVLS KGLNQTM |
| 32 | Stalk Human CD22 | FIG. 2B, 210 | MKVTQPDSNTLTCEVMGPTSPKMRLILKQE NQEARVSRQEKVIQVQAPEAGVWQCLLSEG EEVKMDSKIQVLSKGLNQTM |
| 33 | Transmembrane Domain Human LAG3 | FIG. 2B, 211 | APGALPAGHLLLFLTLGVLSLLLLVTGAFG FHLWRRQWR |
| 34 | Transmembrane Domain Human CD58 | FIG. 2B, 211 | HSRHRYALIPIPLAVITTCIVLYMNGILKC DRKPDRTNSN |
| 35 | Transmembrane Domain Rat CD2 | FIG. 2B, 211 | PLYLIVGVSAGGLLLVFFGALFIFCICKRK KR |
| 36 | Transmembrane Domain Human CD7 | FIG. 2B, 211 | PPRASALPAPPTGSALPDPQTASALPDPPA ASALPAALAVISFLLGLGLGVACVLARTQI KKLCSWRDKNSAACVVYEDMSHSRCNTLSS PNQYQ |

TABLE 3

GPI anchor sequences

| SEQ ID No. | Description | Sequence |
|---|---|---|
| 37 | Human CD59 | GAATTCCTTGAAAATGGTGGGACATCCTTATCAGAGAAAA CAGTTCTTCTGCTGGTGACTCCATTTCTGGCAGCAGCCTG GAGCCTTCATCCC |
| 38 | Human CD59 | EFLENGGTSLSEKTVLLLVTPFLAAAWSLHP |
| 39 | Human CD24 | ACCAATGCCACAACAAAGGCAGCAGGGGGAGCACTCCAGT CAACAGCAAGTTTGTTTGTCGTGTCACTGAGTCTCTTGCA TCTTTATTCA |
| 40 | Human CD24 | TNATTKAAGGALQSTASLFVVSLSLLHLYS |
| 41 | Human CNTN1 (Contactin 1) | GTCTCCCAGGTGAAAATTTCAGGAGCCCCTACCCTCTCCC CATCCCTCCTGGGTTTGCTGCTGCCCGCCTTTGGCATTCT CGTGTATCTGGAGTTC |
| 42 | Human CNTN1 (Contactin 1) | VSQVKISGAPTLSPSLLGLLLPAFGILVYLEF |

TABLE 4

Example 4 sequences

| SEQ ID No. | Description | Sequence |
|---|---|---|
| 43 | $V_L$ Leader exon 1 | ATGGAATCACAGACCCAGGTCCTCATGTTTCTTCTGCT CTGGGTATCTG |
| 44 | $V_L$ intron | GTAAGAAATTTAAAGTATTAAAACCTTTTCAAAGTTTC ATCTTTGTGGTAAGAAATTTGCAATATGTGCCAGTGTG TAATATTTCTTACATAATAAATTTGTGACAGTATGATA AGGACATTTAAATGAAAAATTTCGACTGTTGTTATAAT CTATGTCTGTGTATCTATGAATTTTCACTGCCTATTAA TTATTACAG |
| 45 | $V_L$ exon 2 end of $V_L$ leader sequence | GTGCCTGTGCA |
| 46 | $V_L$ exon 2 | GACATTCAGATGACCCAGTCTCCATCCTCCATGTCTGT GTCTCTGGGAGACACAGTCACTATTACTTGCCGGGCAA GTCAGGACGTTGGGATTTATGTAAACTGGTTCCAGCAG AAACCAGGGAAATCTCCTAGGCGTATGATTTATCGTGC AACGAACTTGGCAGATGGGGTCCCATCAAGGTTCAGCG GCAGTAGGTCTGGATCAGATTATTCTCTCACCATCAGC AGCCTGGAGTCTGAAGATGTGGCAGACTATCACTGTCT ACAGTATGATGAGTATCCATTCACGTTCGGATCCGGGA CGAAGTTGGAAATAAAACGG |
| 47 | $V_L$ exon 2 linker | GGAGGCGGAGGCAGCGGAGGCGGTGGCTCGGGAGGCGG AGGCTCG |
| 48 | $V_H$ exon 2 | CAGGTACAGCTGAAAGAGTCAGGACCTGGTCTGGTGCA GCCCTCACAGACCCTGTCTCTCACCTGCACTGTCTCTG GACTCTCATTAATCAGTTATGGTGTAAGTTGGGCTCGC CAGCCTCCAGGGAAGGGTCTGGAGTGGATTGCAGCAAT |

TABLE 4-continued

Example 4 sequences

| SEQ ID No. | Description | Sequence |
|---|---|---|
| | | ATCAAGTGGTGGAAGCACATATTATAATTCAGTTCTCA CATCTCGACTGAGCATCAGCAGGGACACCTCCAAGAGC CAAGTTTTCTTAAAAATGAACAGTCTGCAAACTGAAGA CACAGCCATTTACTTCTGTACCAGAGAACTCTGGGACT ACTATGATTACTGGGGCCAAGGAGTCATGGTCACAGTC TCCTCA |
| 49 | Exon 2-Rat IgG1 Fc | GCTGAAACAACAGCCCCCAGAAACCCGGGAGGTGATTG CAAGCCTTGTATATGTACAGGCTCAGAAGTATCATCTG TCTTCATCTTCCCCCAAAGCCCAAAGATGTGCTCACC ATCACTCTGACTCCTAAGGTCACGTGTGTTGTGGTAGA CATTAGCCAGGACGATCCCGAGGTCCATTTCAGCTGGT TTGTAGATGACGTGGAAGTCCACACAGCTCAGACTCGA CCACCAGAGGAGCAGTTCAACAGCACTTTCCGCTCAGT CAGTGAACTCCCCATCCTGCACCAGGACTGGCTCAATG GCAGGACGTTCAGATGCAAGGTCACCAGTGCAGCTTTC CCATCCCCATCGAGAAAACCATCTCCAAACCCGAAGG CAGAACACAAGTTCCGCATGTATACACCATGTCACCTA CCAAGGAAGAGATGACCCAGAATGAAGTCAGTATCACC TGCATGGTAAAAGGCTTCTATCCCCCAGACATTTATGT GGAGTGGCAGATGAACGGGCAGCCACAGGAAAACTACA AGAACACTCCACCTACGATGGACACAGATGGGAGTTAC TTCCTCTACAGCAAGCTCAATGTGAAGAAGGAAAAATG GCAGCAGGGAAACACGTTCACGTGTTCTGTGCTGCATG AAGGCCTGCACAACCACCATACTGAGAAGAGTCTCTCC CACTCCCCCGGT |
| 50 | Exon 2 part of mouse MHC I (H2K$^b$) transmembrane domain | AAAGAGCCTCCTCCATCCACTGTCTCCAACATGGCGAC CGTTGCTGTTCTGGTTGTCCTTGGAGCTGCAATAGTCA CTGGAGCTGTGGTGGCTTTTGTGATGAAGATGAGAAGG AGAAACACAG |
| 51 | Intron | GTAGGAAAGGGCAGAGTCTGAGTTTTCTCTCAGCCTCC TTTAGAGTGTGCTCTGCTCATCAATGGGGAACACAGGC ACACCCCACATTGCTACTGTCTCTAACTGGGTCTGCTG TCAGTTCTGGGAACTTCCTAGTGTCAAGATCTTCCTGG AACTCTCACAGCTTTTCTTCTCACAG |
| 52 | Exon 3-part of mouse MHC I (H2K$^b$) transmembrane domain | GTGGAAAAGGAGGGGACTATGCTCTGGCTCCAG |
| 53 | Intron | GTTAGTGTGGGGACAGAGTTGTCCTGGGGACATTGGAG TGAAGTTGGAGATGATGGGAGCTCTGGGAATCCATAAT AGCTCCTCAGAGAAATCTTCTAGGTGCCTGAGTTGTG CCATGAAATGAATATGTACATGTACATATGCATATACA TTTGTTTTGTTTTACCCTAG |
| 54 | Exon 4 - end of mouse MHC I (H2K$^b$) transmembrane domain | GCTCCCAGACCTCTGATCTGTCTCTCCCAGATTGTAAA GGTGACACTCTAGGGTCTGATTGGGGAGGGGCAATGTG GACATGA |
| 55 | V$_L$ leader | MESQTQVLMFLLLWVSGACA |

TABLE 4-continued

Example 4 sequences

| SEQ ID No. | Description | Sequence |
|---|---|---|
| 56 | V$_L$ | DIQMTQSPSSMSVSLGDTVTITCRASQDVGIYVNWFQQ KPGKSPRRMIYRATNLADGVPSRFSGSRSGSDYSLTIS SLESEDVADYHCLQYDEYPFTFGSGTKLEIKR |
| 29 | Linker | GGGGSGGGGSGGGGS |
| 57 | V$_H$ | QVQLKESGPGLVQPSQTLSLTCTVSGLSLISYGVSWAR QPPGKGLEWIAAISSGGSTYYNSVLTSRLSISRDTSKS QVFLKMNSLQTEDTAIYFCTRELWDYYDYWGQGVMVTV SS |
| 58 | Rat IgG1 Fc | AETTAPRNPGGDCKPCICTGSEVSSVFIFPPKPKDVLT ITLTPKVTCVVVDISQDDPEVHFSWFVDDVEVHTAQTR PPEEQFNSTFRSVSELPILHQDWLNGRTFRCKVTSAAF PSPIEKTISKPEGRTQVPHVYTMSPTKEEMTQNEVSIT CMVKGFYPPDIYVEWQMNGQPQENYKNTPPTMDTDGSY FLYSKLNVKKEKWQQGNTFTCSVLHEGLHNHHTEKSLS HSPG |
| 59 | Mouse MHC I (H2K$^b$) transmembrane domain | KEPPPSTVSNMATVAVLVVLGAAIVTGAVVAFVMKMRR RNTGGKGGDYALAPGSQTSDLSLPDCKGDTLGSDWGGA MWT |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112,¶6.

We claim:

1. A genetically modified mouse whose genome comprises a transgene encoding an immunoglobulin-capturing molecule comprising a promoter that expresses the immunoglobulin-capturing molecule in antibody secreting cells, but not in immature B cells or mature B cells,
   wherein the promoter is operably linked to a gene encoding a cell surface tether portion comprising a transmembrane peptide domain; and a gene encoding an immunoglobulin-binding portion comprising one or more immunoglobulin binding domains from a bacterial protein selected from Protein A, Protein G, Protein H, Protein L or a combination thereof, or a single-chain variable fragment (scFv) that specifically binds a conserved epitope of a mouse immunoglobulin heavy chain or light chain constant region,
   wherein the transgene is expressed in antibody-secreting cells which produce immunoglobulin-capturing molecules that bind, retain, and display endogenously produced immunoglobulin molecules at a cell surface of the antibody-secreting cells.

2. The genetically modified mouse of claim 1, wherein the antibody-secreting cells express the immunoglobulin-capturing molecule in vivo, in vitro, or ex vivo.

3. The genetically modified mouse of claim 1, wherein the transmembrane peptide is Major Histocompatibility Class I (MHC I) protein, human Lymphocyte Activation Gene 3, human CD58, rat CD2, or human CD7.

4. The genetically modified mouse of claim 3, wherein the transmembrane peptide is encoded by a nucleotide sequence set forth in one of SEQ ID NOS: 17-20, 33-36 or 59.

5. The genetically modified mouse of claim 1, wherein the immunoglobulin-binding portion comprises a bacterial protein selected from Protein A from *Staphylococcus aureus*, Protein G from group C and G Streptococci, Protein H from *Streptococcus pyogenes*, or Protein L from *Peptostreptococcus magnus*.

6. The genetically modified mouse of claim 1, wherein the immunoglobulin binding portion is encoded by a nucleotide sequence set forth in one of SEQ ID NOS: 8-11 or 24-27.

7. The genetically modified mouse of claim 1, wherein the scFv is expressed as a fusion protein comprising $V_H$ and $V_L$ domains derived from a hybridoma cell line that produces monoclonal antibodies against a heavy chain or light chain constant region of another immunoglobulin molecule.

8. The genetically modified mouse of claim 1, wherein the immunoglobulin-binding portion is encoded by a nucleotide sequence set forth in one of SEQ ID NOS: 43-48.

9. The genetically modified mouse of claim 1, wherein the promoter is selected from B Lymphocyte-Induced Maturation Protein 1, Syndecan 1, Tumor Necrosis Factor Receptor Superfamily Member 17, or Fucosyltransferase 1 genes.

10. The genetically modified mouse of claim 1, wherein the transgene further comprises one or more of: a nucleic acid sequence encoding a signal peptide; a nucleic acid sequence encoding a stalk structure; a nucleic acid sequence encoding a reporter peptide; an IRES sequence; a picornavirus 2A ribosomal skip sequence; or a combination thereof.

11. The genetically modified mouse of claim 10, wherein the reporter peptide comprises a fluorescent peptide.

12. The genetically modified mouse of claim 1, wherein the promoter is a B Lymphocyte-Induced Maturation Protein 1 promoter.

13. The genetically modified mouse of claim 1, wherein the promoter expresses the immunoglobulin-capturing molecule in plasmablasts or plasma cells, but not in immature B cells or mature B cells.

* * * * *

SEQUENCE LISTING

<160> NUMBER OF SEQ ID NOS: 59

<210> SEQ ID NO 1
<211> LENGTH: 55
<212> TYPE: DNA
<213> ORGANISM: Homo sapiens

<400> SEQUENCE: 1
atggacatca gggctcctgc tcagtttctt ggcatcttgt tgctctggtt tccag        55

<210> SEQ ID NO 2
<211> LENGTH: 110
<212> TYPE: DNA
<213> ORGANISM: Homo sapiens

<400> SEQUENCE: 2
gtaaaatgaa ctaaaatggg aatttcactg taagtgttga caggcatttg gggactgtgt   60
tcttttatca tgcttacctt tgtagatatt cattatgtct ccactcctag              110

<210> SEQ ID NO 3
<211> LENGTH: 23
<212> TYPE: DNA
<213> ORGANISM: Homo sapiens

<400> SEQUENCE: 3
gtgccagatg tgacatccag atg                                           23

<210> SEQ ID NO 4
<211> LENGTH: 63
<212> TYPE: DNA
<213> ORGANISM: Artificial Sequence
<220> FEATURE:
<223> OTHER INFORMATION: Leader Exon1/Intron/Exon 2/TagsFLAG+Myc Tags

<400> SEQUENCE: 4
gactacaagg atgacgacga caagggcagc ggcgaacaga agctgatttc ggaggaggac   60
ctg                                                                 63

<210> SEQ ID NO 5
<211> LENGTH: 46
<212> TYPE: DNA
<213> ORGANISM: Homo sapiens

<400> SEQUENCE: 5
atgggatgga gctgtatcat gctcttcttg gcagcaacag ctacag                  46

<210> SEQ ID NO 6
<211> LENGTH: 82
<212> TYPE: DNA
<213> ORGANISM: Homo sapiens

<400> SEQUENCE: 6 gtaagggct cacagtagca ggcttgaggt ctggacatat acatgggtga caatgacatc    60
cactttgcct ttctctccac ag                                            82

<210> SEQ ID NO 7
<211> LENGTH: 23
<212> TYPE: DNA
<213> ORGANISM: Homo sapiens

<400> SEQUENCE: 7
gtgtccactc ccaggtccaa ctg                                           23

<210> SEQ ID NO 8
<211> LENGTH: 369
<212> TYPE: DNA
<213> ORGANISM: Escherichia coli

<400> SEQUENCE: 8

```
ggtaccccag ccgtgaccac ctacaagctc gtcatcaacg aaagacgct caagggcgaa      60
accactacca aggcggtgga tgccgaaacc gccgaaaagg ccttcaagca gtacgctaac     120
gacaatgggg tggacggagt ctggacgtac gatgatgcca ccaagacttt caccgtgacc     180
gaagtgaaca ctccggccgt caccacttat aagctcgtga tcaacgggaa acccctgaag     240
ggagagacta ccacaaaggc cgtggatgct gagactgcag agaaggcgtt caaacagtac     300
gccaacgaca acggcgtgga cggcgtctgg acctacgatg acgccactaa gaccttcact     360
gtgaccgaa                                                            369
```

<210> SEQ ID NO 9
<211> LENGTH: 621
<212> TYPE: DNA
<213> ORGANISM: Escherichia coli

<400> SEQUENCE: 9

```
atagatgaaa ttttagctgc attacctaag actgacactt acaaattaat ccttaatggt      60
aaaacattga aggcgaaac aactactgaa gctgttgatg ctgctactgc agaaaaagtc     120
ttcaaacaat acgctaacga caacggtgtt gacggtgaat ggacttacga cgatgcgact     180
aagacctta cagttactga aaaccagaa gtgatcgatg cgtctgaatt aacaccagcc     240
gtgacaactt acaaacttgt tattaatggt aaaacattga aggcgaaac aactactgaa     300
gctgttgatg ctgctactgc agaaaaagtc ttcaaacaat acgctaacga caacggtgtt     360
gacggtgaat ggacttacga cgatgcgact aagacctta cagttactga aaaccagaa     420
gtgatcgatg cgtctgaatt aacaccagcc gtgacaactt acaaacttgt tattaatggt     480
aaaacattga aggcgaaac aactactaaa gcagtagacg cagaaactgc agaaaaagcc     540
ttcaaacaat acgctaacga caacggtgtt gatggtgttt ggacttatga tgatgcgact     600
aagacctta cggtaactga a                                               621
```

<210> SEQ ID NO 10
<211> LENGTH: 741
<212> TYPE: DNA
<213> ORGANISM: Escherichia coli

<400> SEQUENCE: 10

```
gtggataaca agttcaacaa ggaacagcag aacgcctttt acgagattct gcatctgccc      60
aacctgaatg aggaacagcg gaacgcattc attcagtctc tgaaggatga tcctagccag     120
tcggccaacc tcctggctga agcaaagaag ctgaacgatg cccaagcgcc caagtggac     180
aacaagttta caaggagca gcagaatgct ttctacgaga tcctgcacct cccgaatctg     240
aacgaggagc agagaaacgc cttcatccaa tcactgaagg acgaccgtc acagtccgcc     300
aaccttctgg cggaagccaa gaaactgaac gacgcccagg cgccaaaggt ggacggatcc     360
gggtccggca gcggtacccc agccgtgacc acctacaagc tcgtcatcaa cggaaagacg     420
ctcaagggcg aaaccactac caaggcggtg atgccgaaa ccgccgaaaa ggccttcaag     480
cagtacgcta acgacaatgg ggtggacgga gtctggacgt acgatgatgc caccaagact     540
```

```
ttcaccgtga ccgaagtgaa cactccggcc gtcaccactt ataagctcgt gatcaacggg    600
aaaaccctga agggagagac taccacaaag gccgtggatg ctgagactgc agagaaggcg    660
ttcaaacagt acgccaacga caacggcgtg gacggcgtct ggacctacga tgacgccact    720
aagaccttca ctgtgaccga a                                              741
```

<210> SEQ ID NO 11
<211> LENGTH: 1681
<212> TYPE: DNA
<213> ORGANISM: Escherichia coli

<400> SEQUENCE: 11

```
aaacctcaac gccgatcagc gcaatggttt cattcagtcc ctgaaggacg atccgagcca     60
gtcagctaac gtgctcgggg aggcccaaaa gctgaatgac tcccaggcgc cgaaggccga    120
cgcccagcaa acaacttca acaaggatca gcaatccgcc ttctatgaaa tcctgaatat     180
gcctaacctg aacgaagctc agcggaacgg gttcatccag agccttaagg acgaccctag    240
ccagtccacc aacgtgctgg gggaggccaa gaaacttaac gaatcccagg ccccgaaggc    300
ggacaacaac tttaacaagg aacagcagaa cgccttttac gagatcctca acatgccgaa    360
cctcaacgag aacagcgca acggtttcat ccagtccctg aaggacgatc catcccagtc    420
cgccaacctg ttgagcgagg cgaagaagct gaatgagtcc caagcccca aggctgacaa    480 caagttcaat aaggaacaac agaatgcctt ctacgaaatt ctgcacttgc caatctgaa    540 cgaggagcag cgcaacggct tcatccaatc tctgaaagac gacccgtcgc agtcggccaa    600
cttgctggcc gaagccaaga agctcaacga cgctcaggcc cctaaggccg acaacaagtt    660
caacaaagag caacagaacg cgttctacga gattctccac ttgccgaacc tgaccgaaga    720
acaacggaac ggattcattc agagcctgaa ggatgacccc tcggtgtcaa aggagatcct    780
ggcagaagcc aaaaagctga cgatgcccca ggcaccaaag gaagaggaca caacaagcc    840 gggcgacccg aggatctccg aagccactga tgggctgtcc gattttctga agtcacagac    900
tcctgctgag gacaccgtga agtccatcga gctcgccgag gccaaggtgc tggccaaccg    960
ggagctggat aagtacggag tgtccgacta ctacaaaaac ctgattaaca acgccaagac   1020
tgtggaagga gtgaaggcat tgatcgatga atcctggcg gcgctcccaa aaaccgacac   1080
ctacaaactg attctcaacg aaagacgct gaaggggga actaccaccg aagcggtgga   1140
cgccgccacc gccgaaaagg tgtttaagca gtatgctaac gacaacggtg tcgacggaga   1200
gtggacctac gacgacgcca ctaagacttt caccgtgacc gagaagcccg aggtcatcga   1260
cgcgagcgag ctcactcccg ccgtgaccac ctacaagctg gtcatcaatg aaagactct   1320 gaagggcgaa actactactg aagccgtgga tgcggcaacc gccgagaaag tgttcaagca   1380
atacgcaaac gataacgggg tggacggaga gtggacctac gacgatgcca caaagacctt   1440
caccgtcacc gaaaagcccg aagtgatcga cgcttccgaa ctgacgccgg ccgtgacaac   1500
ttacaagctc gtcattaacg aaagaccct taagggcgaa accacgacca aggcagtgga   1560
cgccgaaact gccgagaagg cgttcaagca gtacgccaac gacaacggcg tggacggagt   1620
gtggacttac gatgatgcga ccaagacgtt cactgtgacc gagatggtca ccgaagtgcc   1680
g                                                                 1681
```

<210> SEQ ID NO 12
<211> LENGTH: 18
<212> TYPE: DNA
<213> ORGANISM: Artificial Sequence

```
<220> FEATURE:
<223> OTHER INFORMATION: Gly/Ser linker

<400> SEQUENCE: 12
ggatccggct ccggatcc                                                   18

<210> SEQ ID NO 13
<211> LENGTH: 45
<212> TYPE: DNA
<213> ORGANISM: Artificial Sequence
<220> FEATURE:
<223> OTHER INFORMATION: Gly/Ser linker

<400> SEQUENCE: 13
ggaggcggag gcagcggagg cggtggctcg ggaggcggag gctcg               45

<210> SEQ ID NO 14
<211> LENGTH: 243
<212> TYPE: DNA
<213> ORGANISM: Rattus rattus

<400> SEQUENCE: 14
gagatggtgt ccaagccgat gatctactgg gagtgttcca acgcgactct gacctgtgaa    60
gtgctggagg gaaccgacgt ggaactgaag ctgtaccagg gtaaagaaca tctgcggtcg   120
ttgcgccaaa agaccatgag ctaccagtgg accaacttgc gggcgccttt caagtgcaaa   180
gccgtcaata gagtgtccca ggagagcgaa atggaggtcg tgaactgccc cgaaaaggga   240
ctg                                                                 243

<210> SEQ ID NO 15
<211> LENGTH: 561
<212> TYPE: DNA
<213> ORGANISM: Rattus rattus

<400> SEQUENCE: 15
tcaacttcca tcaccgccta caagagcgag ggagagagcg ccgagttttc cttcccctg     60 aacctgggcg aagaaagcct ccagggagaa ctgcgctgga aggcagaaaa ggccccaagc   120
tctcagtcct ggatcacctt cagcctgaag aaccagaagg tgtccgtgca agagtccact   180
tcaaacccga agttccagct ctccgaaacc ctccctctga ccctgcaaat ccctcaagtg   240
tcgctgcaat tcgcggggag cggaaatctg actctgactc ttgaccgggg catcttgtac   300
caggaggtga acctggtggt catgaaggtg acccagcccg atagcaacac cctgacctgt   360
gaagtgatgg gacccacgtc cccgaagatg cggctcattc tgaagcagga gaaccaggag   420
gctcgggtgt ccagacagga aaaggtcatc caagtgcagg ccccggaagc cggcgtgtgg   480
cagtgcctgc tgtccgaggg agaggaagtc aagatggact cgaaaatcca ggtgctgtcc   540
aaagggctga accagactat g                                             561

<210> SEQ ID NO 16
<211> LENGTH: 1638
<212> TYPE: DNA
<213> ORGANISM: Homo sapiens

<400> SEQUENCE: 16
gaaaggcctt ttccacctca tatccagctc cctccagaaa ttcaagagtc ccaggaagtc    60
actctgacct gcttgctgaa tttctcctgc tatgggtatc cgatccaatt gcagtggctc   120
ctagaggggg ttccaatgag gcaggctgct gtcacctcga cctccttgac catcaagtct   180
```

```
gtcttcaccc ggagcgagct caagttctcc ccacagtgga gtcaccatgg gaagattgtg      240
acctgccagc ttcaggatgc agatgggaag ttcctctcca atgacacggt gcagctgaac      300
gtgaagcaca ccccgaagtt ggagatcaag gtcactccca gtgatgccat agtgagggag      360
ggggactctg tgaccatgac ctgcgaggtc agcagcagca cccggagtta cacgacggta      420
tcctggctca aggatgggac ctcgctgaag aagcagaata cattcacgct aaacctgcgc      480
gaagtgacca aggaccagag tgggaagtac tgctgtcagg tctccaatga cgtgggcccg      540
ggaaggtcgg aagaagtgtt cctgcaagtg cagtatgccc cggaaccttc cacggttcag      600
atcctccact caccggctgt ggagggaagt caagtcgagt ttctttgcat gtcactggcc      660
aatcctcttc aacaaattac acgtggtac cacaatggga agaaatgca gggaaggaca       720 gaggagaaag tccacatccc aaagatcctc cctggcacg ctgggactta ttcctgtgtg       780
gcagaaaaca ttcttggtac tggacagagg ggcccgggag ctgagctgga tgtccagtat      840
cctcccaaga aggtgaccac agtgattcaa aaccccatgc cgattcgaga aggagacaca      900
gtgacccttt cctgtaacta caattccagt aaccccagtt taccccggta tgaatggaaa      960
ccccatggcg cctgggagga gccatcgctt ggggtgctga agatccaaaa cgttggctgg     1020
gacaacacaa ccatcgcctg cgcagcttgt aatagttggt gctcgtgggc ctcccctgtc     1080
gccctgaatg tccagtatgc cccccgagac gtgagggtcc ggaaaatcaa gccccttccc     1140
gagattcact ctggaaactc ggtcagcctc caatgtgact tctcaagcag ccaccccaaa     1200
gaagtccagt tcttctggga gaaaaatggc aggcttctgg ggaagaaag ccagctgaat      1260 tttgactcca tctccccaga agatgctggg agttacagct gctgggtgaa caactccata     1320
ggacagacag cgtccaaggc ctggacactt gaagtgctgt atgcacccag gaggctgcgt     1380
gtgtccatga gccgggggga ccaagtgatg aggggaagaa gtgcaaccct gacctgtgag     1440
agcgacgcca accctcccgt ctcccactac acctggtttg actggaataa ccaaagcctc     1500
ccctaccaca gccagaagct gagattggag ccggtgaagg tccagcactc gggtgcctac     1560
tggtgccagg ggaccaacag tgtgggcaag ggccgttcgc tctcagcac cctcaccgtc      1620 tactatagcc ggagacc                                                    1638

<210> SEQ ID NO 17
<211> LENGTH: 120
<212> TYPE: DNA
<213> ORGANISM: Homo sapiens

<400> SEQUENCE: 17
gcgcctggag cgctgccggc cggtcatctg ttgttgttcc tgaccctggg ggtgctgtca       60
ctgctgctgc tcgtgaccgg ggcattcggt ttccacctgt ggagaaggca gtggcggtag      120

<210> SEQ ID NO 18
<211> LENGTH: 123
<212> TYPE: DNA
<213> ORGANISM: Homo sapiens

<400> SEQUENCE: 18
cattcccggc accgctacgc gctgattccg attcctctgg ccgtgatcac cacctgtatc       60
gtgctctaca tgaacggtat cctgaaatgc gacagaaagc ccgacaggac taacagcaat      120
tag                                                                    123

<210> SEQ ID NO 19
<211> LENGTH: 99
```

```
<212> TYPE: DNA
<213> ORGANISM: Rattus rattus

<400> SEQUENCE: 19
ccgctgtacc tgatcgtggg ggtgtcagcc ggcggtctgc tgctcgtgtt cttcggggca    60
ctgttcatct tctgcatttg caagaggaag aagcggtag                           99

<210> SEQ ID NO 20
<211> LENGTH: 288
<212> TYPE: DNA
<213> ORGANISM: Homo sapiens

<400> SEQUENCE: 20
ccaccccggg cgtccgcact gccggcgccc cctaccggaa gcgcgctgcc cgatccgcaa    60
accgccagcg ccctgcctga cccgcccgcg gctagcgcct tgcctgccgc actggccgtg   120
atttcattcc tgctgggtct ggggctcggg gtggcctgcg tgttggcacg gactcagatc   180
aagaagctgt gctcctggag agacaaaaac tccgccgcct gtgtggtgta cgaggacatg   240
tcacactcga ggtgcaatac cctgtcctcg ccgaaccagt accagtag                288

<210> SEQ ID NO 21
<211> LENGTH: 23
<212> TYPE: PRT
<213> ORGANISM: Homo sapiens

<400> SEQUENCE: 21

Met Gly Trp Ser Cys Ile Met Leu Phe Leu Ala Ala Thr Ala Thr Gly
1               5                   10                  15

Val His Ser Gln Val Gln Leu
            20

<210> SEQ ID NO 22
<211> LENGTH: 21
<212> TYPE: PRT
<213> ORGANISM: Artificial Sequence
<220> FEATURE:
<223> OTHER INFORMATION: Leader Exon1/Intron/Exon 2/TagsFLAG+Myc Tags

<400> SEQUENCE: 22

Asp Tyr Lys Asp Asp Asp Asp Lys Gly Ser Gly Glu Gln Lys Leu Ile
1               5                   10                  15

Ser Glu Glu Asp Leu
            20

<210> SEQ ID NO 23
<211> LENGTH: 26
<212> TYPE: PRT
<213> ORGANISM: Homo sapiens

<400> SEQUENCE: 23

Met Asp Ile Arg Ala Pro Ala Gln Phe Leu Gly Ile Leu Leu Leu Trp
1               5                   10                  15

Phe Pro Gly Ala Arg Cys Asp Ile Gln Met
            20                  25

<210> SEQ ID NO 24
<211> LENGTH: 123
<212> TYPE: PRT
<213> ORGANISM: Escherichia coli

<400> SEQUENCE: 24
```

```
Gly Thr Pro Ala Val Thr Thr Tyr Lys Leu Val Ile Asn Gly Lys Thr
 1               5                  10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly Val Trp
        35                  40                  45

Thr Tyr Asp Asp Ala Thr Lys Thr Phe Thr Val Thr Glu Val Asn Thr
 50                  55                  60

Pro Ala Val Thr Thr Tyr Lys Leu Val Ile Asn Gly Lys Thr Leu Lys
 65                  70                  75                  80

Gly Glu Thr Thr Thr Lys Ala Val Asp Ala Glu Thr Ala Glu Lys Ala
                85                  90                  95

Phe Lys Gln Tyr Ala Asn Asp Asn Gly Val Asp Gly Val Trp Thr Tyr
            100                 105                 110

Asp Asp Ala Thr Lys Thr Phe Thr Val Thr Glu
            115                 120
```

<210> SEQ ID NO 25
<211> LENGTH: 207
<212> TYPE: PRT
<213> ORGANISM: Escherichia coli

<400> SEQUENCE: 25

```
Ile Asp Glu Ile Leu Ala Ala Leu Pro Lys Thr Asp Thr Tyr Lys Leu
 1               5                  10                  15

Ile Leu Asn Gly Lys Thr Leu Lys Gly Glu Thr Thr Thr Glu Ala Val
            20                  25                  30

Asp Ala Ala Thr Ala Glu Lys Val Phe Lys Gln Tyr Ala Asn Asp Asn
        35                  40                  45

Gly Val Asp Gly Glu Trp Thr Tyr Asp Asp Ala Thr Lys Thr Phe Thr
 50                  55                  60

Val Thr Glu Lys Pro Glu Val Ile Asp Ala Ser Glu Leu Thr Pro Ala
 65                  70                  75                  80

Val Thr Thr Tyr Lys Leu Val Ile Asn Gly Lys Thr Leu Lys Gly Glu
                85                  90                  95

Thr Thr Thr Glu Ala Val Asp Ala Ala Thr Ala Glu Lys Val Phe Lys
            100                 105                 110

Gln Tyr Ala Asn Asp Asn Gly Val Asp Gly Glu Trp Thr Tyr Asp Asp
            115                 120                 125

Ala Thr Lys Thr Phe Thr Val Thr Glu Lys Pro Glu Val Ile Asp Ala
            130                 135                 140

Ser Glu Leu Thr Pro Ala Val Thr Thr Tyr Lys Leu Val Ile Asn Gly
145                 150                 155                 160

Lys Thr Leu Lys Gly Glu Thr Thr Thr Lys Ala Val Asp Ala Glu Thr
                165                 170                 175

Ala Glu Lys Ala Phe Lys Gln Tyr Ala Asn Asp Asn Gly Val Asp Gly
            180                 185                 190

Val Trp Thr Tyr Asp Asp Ala Thr Lys Thr Phe Thr Val Thr Glu
            195                 200                 205
```

<210> SEQ ID NO 26
<211> LENGTH: 247
<212> TYPE: PRT
<213> ORGANISM: Escherichia coli

<400> SEQUENCE: 26

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys Val Asp Gly Ser Gly Ser Gly Thr Pro Ala
        115                 120                 125

Val Thr Thr Tyr Lys Leu Val Ile Asn Gly Lys Thr Leu Lys Gly Glu
        130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu Val Asn Thr Pro Ala Val Thr
            180                 185                 190

Thr Tyr Lys Leu Val Ile Asn Gly Lys Thr Leu Lys Gly Glu Thr Thr
        195                 200                 205

Thr Lys Ala Val Asp Ala Glu Thr Ala Glu Lys Ala Phe Lys Gln Tyr
210                 215                 220

Ala Asn Asp Asn Gly Val Asp Gly Val Trp Thr Tyr Asp Asp Ala Thr
225                 230                 235                 240

Lys Thr Phe Thr Val Thr Glu
                245

<210> SEQ ID NO 27
<211> LENGTH: 581
<212> TYPE: PRT
<213> ORGANISM: Escherichia coli

<400> SEQUENCE: 27

Ala Asn Ala Ala Gln His Asp Glu Ala Gln Gln Asn Ala Phe Tyr Gln
1               5                   10                  15

Val Leu Asn Met Pro Asn Leu Asn Ala Asp Gln Arg Asn Gly Phe Ile
            20                  25                  30

Gln Ser Leu Lys Asp Asp Pro Ser Gln Ser Ala Asn Val Leu Gly Glu
        35                  40                  45

Ala Gln Lys Leu Asn Asp Ser Gln Ala Pro Lys Ala Asp Ala Gln Gln
50                  55                  60

Asn Asn Phe Asn Lys Asp Gln Gln Ser Ala Phe Tyr Glu Ile Leu Asn
65                  70                  75                  80

Met Pro Asn Leu Asn Glu Ala Gln Arg Asn Gly Phe Ile Gln Ser Leu
                85                  90                  95

Lys Asp Asp Pro Ser Gln Ser Thr Asn Val Leu Gly Glu Ala Lys Lys
            100                 105                 110

Leu Asn Glu Ser Gln Ala Pro Lys Ala Asp Asn Asn Phe Asn Lys Glu
        115                 120                 125
```

```
Gln Gln Asn Ala Phe Tyr Glu Ile Leu Asn Met Pro Asn Leu Asn Glu
        130                 135                 140

Glu Gln Arg Asn Gly Phe Ile Gln Ser Leu Lys Asp Asp Pro Ser Gln
145                 150                 155                 160

Ser Ala Asn Leu Leu Ser Glu Ala Lys Lys Leu Asn Glu Ser Gln Ala
                165                 170                 175

Pro Lys Ala Asp Asn Lys Phe Asn Lys Glu Gln Gln Asn Ala Phe Tyr
                180                 185                 190

Glu Ile Leu His Leu Pro Asn Leu Asn Glu Glu Gln Arg Asn Gly Phe
            195                 200                 205

Ile Gln Ser Leu Lys Asp Asp Pro Ser Gln Ser Ala Asn Leu Leu Ala
210                 215                 220

Glu Ala Lys Lys Leu Asn Asp Ala Gln Ala Pro Lys Ala Asp Asn Lys
225                 230                 235                 240

Phe Asn Lys Glu Gln Gln Asn Ala Phe Tyr Glu Ile Leu His Leu Pro
                245                 250                 255

Asn Leu Thr Glu Glu Gln Arg Asn Gly Phe Ile Gln Ser Leu Lys Asp
            260                 265                 270

Asp Pro Ser Val Ser Lys Glu Ile Leu Ala Glu Ala Lys Lys Leu Asn
            275                 280                 285

Asp Ala Gln Ala Pro Lys Glu Glu Asp Asn Asn Lys Pro Gly Asp Pro
290                 295                 300

Arg Ile Ser Glu Ala Thr Asp Gly Leu Ser Asp Phe Leu Lys Ser Gln
305                 310                 315                 320

Thr Pro Ala Glu Asp Thr Val Lys Ser Ile Glu Leu Ala Glu Ala Lys
                325                 330                 335

Val Leu Ala Asn Arg Glu Leu Asp Lys Tyr Gly Val Ser Asp Tyr Tyr
            340                 345                 350

Lys Asn Leu Ile Asn Asn Ala Lys Thr Val Glu Gly Val Lys Ala Leu
            355                 360                 365

Ile Asp Glu Ile Leu Ala Ala Leu Pro Lys Thr Asp Thr Tyr Lys Leu
370                 375                 380

Ile Leu Asn Gly Lys Thr Leu Lys Gly Glu Thr Thr Thr Glu Ala Val
385                 390                 395                 400

Asp Ala Ala Thr Ala Glu Lys Val Phe Lys Gln Tyr Ala Asn Asp Asn
                405                 410                 415

Gly Val Asp Gly Glu Trp Thr Tyr Asp Asp Ala Thr Lys Thr Phe Thr
            420                 425                 430

Val Thr Glu Lys Pro Glu Val Ile Asp Ala Ser Glu Leu Thr Pro Ala
            435                 440                 445

Val Thr Thr Tyr Lys Leu Val Ile Asn Gly Lys Thr Leu Lys Gly Glu
            450                 455                 460

Thr Thr Thr Glu Ala Val Asp Ala Ala Thr Ala Glu Lys Val Phe Lys
465                 470                 475                 480

Gln Tyr Ala Asn Asp Asn Gly Val Asp Gly Glu Trp Thr Tyr Asp Asp
                485                 490                 495

Ala Thr Lys Thr Phe Thr Val Thr Glu Lys Pro Glu Val Ile Asp Ala
                500                 505                 510

Ser Glu Leu Thr Pro Ala Val Thr Thr Tyr Lys Leu Val Ile Asn Gly
            515                 520                 525

Lys Thr Leu Lys Gly Glu Thr Thr Thr Lys Ala Val Asp Ala Glu Thr
            530                 535                 540
```

```
Ala Glu Lys Ala Phe Lys Gln Tyr Ala Asn Asp Asn Gly Val Asp Gly
545                 550                 555                 560

Val Trp Thr Tyr Asp Asp Ala Thr Lys Thr Phe Thr Val Thr Glu Met
                565                 570                 575

Val Thr Glu Val Pro
            580

<210> SEQ ID NO 28
<211> LENGTH: 6
<212> TYPE: PRT
<213> ORGANISM: Artificial Sequence
<220> FEATURE:
<223> OTHER INFORMATION: Gly/Ser linker

<400> SEQUENCE: 28

Gly Ser Gly Ser Gly Ser
1               5

<210> SEQ ID NO 29
<211> LENGTH: 15
<212> TYPE: PRT
<213> ORGANISM: Artificial Sequence
<220> FEATURE:
<223> OTHER INFORMATION: Gly/Ser Linker

<400> SEQUENCE: 29

Gly Gly Gly Gly Ser Gly Gly Gly Gly Ser Gly Gly Gly Gly Ser
1               5                   10                  15

<210> SEQ ID NO 30
<211> LENGTH: 81
<212> TYPE: PRT
<213> ORGANISM: Rattus rattus

<400> SEQUENCE: 30

Glu Met Val Ser Lys Pro Met Ile Tyr Trp Glu Cys Ser Asn Ala Thr
1               5                   10                  15

Leu Thr Cys Glu Val Leu Glu Gly Thr Asp Val Glu Leu Lys Leu Tyr
            20                  25                  30

Gln Gly Lys Glu His Leu Arg Ser Leu Arg Gln Lys Thr Met Ser Tyr
        35                  40                  45

Gln Trp Thr Asn Leu Arg Ala Pro Phe Lys Cys Lys Ala Val Asn Arg
    50                  55                  60

Val Ser Gln Glu Ser Glu Met Glu Val Val Asn Cys Pro Glu Lys Gly
65                  70                  75                  80

Leu

<210> SEQ ID NO 31
<211> LENGTH: 187
<212> TYPE: PRT
<213> ORGANISM: Rattus rattus

<400> SEQUENCE: 31

Ser Thr Ser Ile Thr Ala Tyr Lys Ser Glu Gly Glu Ser Ala Glu Phe
1               5                   10                  15

Ser Phe Pro Leu Asn Leu Gly Glu Glu Ser Leu Gln Gly Glu Leu Arg
            20                  25                  30

Trp Lys Ala Glu Lys Ala Pro Ser Ser Gln Ser Trp Ile Thr Phe Ser
        35                  40                  45

Leu Lys Asn Gln Lys Val Ser Val Gln Lys Ser Thr Ser Asn Pro Lys
    50                  55                  60
```

Phe Gln Leu Ser Glu Thr Leu Pro Leu Thr Leu Gln Ile Pro Gln Val
 65                  70                  75                  80

Ser Leu Gln Phe Ala Gly Ser Gly Asn Leu Thr Leu Thr Leu Asp Arg
                 85                  90                  95

Gly Ile Leu Tyr Gln Glu Val Asn Leu Val Val Met Lys Val Thr Gln
            100                 105                 110

Pro Asp Ser Asn Thr Leu Thr Cys Glu Val Met Gly Pro Thr Ser Pro
        115                 120                 125

Lys Met Arg Leu Ile Leu Lys Gln Glu Asn Gln Glu Ala Arg Val Ser
    130                 135                 140

Arg Gln Glu Lys Val Ile Gln Val Gln Ala Pro Glu Ala Gly Val Trp
145                 150                 155                 160

Gln Cys Leu Leu Ser Glu Gly Glu Val Lys Met Asp Ser Lys Ile
                165                 170                 175

Gln Val Leu Ser Lys Gly Leu Asn Gln Thr Met
            180                 185

<210> SEQ ID NO 32
<211> LENGTH: 80
<212> TYPE: PRT
<213> ORGANISM: Homo sapiens

<400> SEQUENCE: 32

Met Lys Val Thr Gln Pro Asp Ser Asn Thr Leu Thr Cys Glu Val Met
  1               5                  10                  15

Gly Pro Thr Ser Pro Lys Met Arg Leu Ile Leu Lys Gln Glu Asn Gln
                 20                  25                  30

Glu Ala Arg Val Ser Arg Gln Glu Lys Val Ile Gln Val Gln Ala Pro
             35                  40                  45

Glu Ala Gly Val Trp Gln Cys Leu Leu Ser Glu Gly Glu Val Lys
         50                  55                  60

Met Asp Ser Lys Ile Gln Val Leu Ser Lys Gly Leu Asn Gln Thr Met
 65                  70                  75                  80

<210> SEQ ID NO 33
<211> LENGTH: 39
<212> TYPE: PRT
<213> ORGANISM: Homo sapiens

<400> SEQUENCE: 33

Ala Pro Gly Ala Leu Pro Ala Gly His Leu Leu Phe Leu Thr Leu
  1               5                  10                  15

Gly Val Leu Ser Leu Leu Leu Val Thr Gly Ala Phe Gly Phe His
                 20                  25                  30

Leu Trp Arg Arg Gln Trp Arg
            35

<210> SEQ ID NO 34
<211> LENGTH: 40
<212> TYPE: PRT
<213> ORGANISM: Homo sapiens

<400> SEQUENCE: 34

His Ser Arg His Arg Tyr Ala Leu Ile Pro Ile Pro Leu Ala Val Ile
  1               5                  10                  15

Thr Thr Cys Ile Val Leu Tyr Met Asn Gly Ile Leu Lys Cys Asp Arg
                 20                  25                  30

```
Lys Pro Asp Arg Thr Asn Ser Asn
        35                  40
```

<210> SEQ ID NO 35
<211> LENGTH: 32
<212> TYPE: PRT
<213> ORGANISM: Rattus rattus

<400> SEQUENCE: 35

```
Pro Leu Tyr Leu Ile Val Gly Val Ser Ala Gly Gly Leu Leu Val
1               5                   10                  15

Phe Phe Gly Ala Leu Phe Ile Phe Cys Ile Cys Lys Arg Lys Lys Arg
            20                  25                  30
```

<210> SEQ ID NO 36
<211> LENGTH: 95
<212> TYPE: PRT
<213> ORGANISM: Homo sapiens

<400> SEQUENCE: 36

```
Pro Pro Arg Ala Ser Ala Leu Pro Ala Pro Pro Thr Gly Ser Ala Leu
1               5                   10                  15

Pro Asp Pro Gln Thr Ala Ser Ala Leu Pro Pro Ala Ala Ser
            20                  25                  30

Ala Leu Pro Ala Ala Leu Ala Val Ile Ser Phe Leu Leu Gly Leu Gly
            35                  40                  45

Leu Gly Val Ala Cys Val Leu Ala Arg Thr Gln Ile Lys Lys Leu Cys
        50                  55                  60

Ser Trp Arg Asp Lys Asn Ser Ala Ala Cys Val Val Tyr Glu Asp Met
65                  70                  75                  80

Ser His Ser Arg Cys Asn Thr Leu Ser Ser Pro Asn Gln Tyr Gln
                85                  90                  95
```

<210> SEQ ID NO 37
<211> LENGTH: 93
<212> TYPE: DNA
<213> ORGANISM: Homo sapiens

<400> SEQUENCE: 37

```
gaattccttg aaaatggtgg acatccttta tcagagaaaa cagttcttct gctggtgact    60
ccatttctgg cagcagcctg gagccttcat ccc                                 93
```

<210> SEQ ID NO 38
<211> LENGTH: 31
<212> TYPE: PRT
<213> ORGANISM: Homo sapiens

<400> SEQUENCE: 38

```
Glu Phe Leu Glu Asn Gly Gly Thr Ser Leu Ser Glu Lys Thr Val Leu
1               5                   10                  15

Leu Leu Val Thr Pro Phe Leu Ala Ala Ala Trp Ser Leu His Pro
            20                  25                  30
```

<210> SEQ ID NO 39
<211> LENGTH: 90
<212> TYPE: DNA
<213> ORGANISM: Homo sapiens

<400> SEQUENCE: 39

```
accaatgcca caacaaaggc agcagggggga gcactccagt caacagcaag tttgtttgtc    60
```

```
gtgtcactga gtctcttgca tctttattca                                           90
```

<210> SEQ ID NO 40
<211> LENGTH: 30
<212> TYPE: PRT
<213> ORGANISM: Homo sapiens

<400> SEQUENCE: 40

```
Thr Asn Ala Thr Thr Lys Ala Ala Gly Gly Ala Leu Gln Ser Thr Ala
1               5                   10                  15

Ser Leu Phe Val Val Ser Leu Ser Leu Leu His Leu Tyr Ser
            20                  25                  30
```

<210> SEQ ID NO 41
<211> LENGTH: 96
<212> TYPE: DNA
<213> ORGANISM: Homo sapiens

<400> SEQUENCE: 41

```
gtctcccagg tgaaaatttc aggagcccct accctctccc catccctcct gggtttgctg         60
ctgcccgcct ttggcattct cgtgtatctg gagttc                                   96
```

<210> SEQ ID NO 42
<211> LENGTH: 32
<212> TYPE: PRT
<213> ORGANISM: Homo sapiens

<400> SEQUENCE: 42

```
Val Ser Gln Val Lys Ile Ser Gly Ala Pro Thr Leu Ser Pro Ser Leu
1               5                   10                  15

Leu Gly Leu Leu Leu Pro Ala Phe Gly Ile Leu Val Tyr Leu Glu Phe
            20                  25                  30
```

<210> SEQ ID NO 43
<211> LENGTH: 49
<212> TYPE: DNA
<213> ORGANISM: Homo sapiens

<400> SEQUENCE: 43

```
atggaatcac agacccaggt cctcatgttt cttctgctct gggtatctg                     49
```

<210> SEQ ID NO 44
<211> LENGTH: 199
<212> TYPE: DNA
<213> ORGANISM: Homo sapiens

<400> SEQUENCE: 44

```
gtaagaaatt taaagtatta aaaccttttc aaagtttcat ctttgtggta agaaatttgc         60
aatatgtgcc agtgtgtaat atttcttaca taataaattt gtgacagtat gataaggaca        120
tttaaatgaa aaatttcgac tgttgttata atctatgtct gtgtatctat gaattttcac        180
tgcctattaa ttattacag                                                    199
```

<210> SEQ ID NO 45
<211> LENGTH: 11
<212> TYPE: DNA
<213> ORGANISM: Homo sapiens

<400> SEQUENCE: 45

```
gtgcctgtgc a                                                              11
```

```
<210> SEQ ID NO 46
<211> LENGTH: 324
<212> TYPE: DNA
<213> ORGANISM: Homo sapiens

<400> SEQUENCE: 46
gacattcaga tgacccagtc tccatcctcc atgtctgtgt ctctgggaga cacagtcact    60
attacttgcc gggcaagtca ggacgttggg atttatgtaa actggttcca gcagaaacca   120
gggaaatctc ctaggcgtat gatttatcgt gcaacgaact tggcagatgg ggtcccatca   180
aggttcagcg gcagtaggtc tggatcagat tattctctca ccatcagcag cctggagtct   240
gaagatgtgg cagactatca ctgtctacag tatgatgagt atccattcac gttcggatcc   300
gggacgaagt tggaaataaa acgg                                          324

<210> SEQ ID NO 47
<211> LENGTH: 45
<212> TYPE: DNA
<213> ORGANISM: Homo sapiens

<400> SEQUENCE: 47
ggaggcggag gcagcggagg cggtggctcg ggaggcggag gctcg                    45

<210> SEQ ID NO 48
<211> LENGTH: 348
<212> TYPE: DNA
<213> ORGANISM: Homo sapiens

<400> SEQUENCE: 48
caggtacagc tgaaagagtc aggacctggt ctggtgcagc cctcacagac cctgtctctc    60
acctgcactg tctctggact ctcattaatc agttatggtg taagttgggc tcgccagcct   120
ccagggaagg gtctggagtg gattgcagca atatcaagtg gtggaagcac atattataat   180
tcagttctca catctcgact gagcatcagc agggacacct ccaagagcca agttttctta   240
aaaatgaaca gtctgcaaac tgaagacaca gccatttact tctgtaccag agaactctgg   300
gactactatg attactgggg ccaaggagtc atggtcacag tctcctca                348

<210> SEQ ID NO 49
<211> LENGTH: 696
<212> TYPE: DNA
<213> ORGANISM: Rattus rattus

<400> SEQUENCE: 49
gctgaaacaa cagcccccag aaacccggga ggtgattgca agccttgtat atgtacaggc    60
tcagaagtat catctgtctt catcttcccc ccaaagccca agatgtgct caccatcact    120 ctgactccta aggtcacgtg tgttgtggta gacattagcc aggacgatcc cgaggtccat   180
ttcagctggt ttgtagatga cgtggaagtc cacacagctc agactcgacc accagaggag   240
cagttcaaca gcactttccg ctcagtcagt gaactcccca tcctgcacca ggactggctc   300
aatggcagga cgttcagatg caaggtcacc agtgcagctt tcccatcccc catcgagaaa   360
accatctcca aacccgaagg cagaacacaa gttccgcatg tatacaccat gtcacctacc   420
aaggaagaga tgacccagaa tgaagtcagt atcacctgca tggtaaaagg cttctatccc   480
ccagacattt atgtggagtg gcagatgaac gggcagccac aggaaaacta caagaacact   540
ccacctacga tggacacaga tgggagttac ttcctctaca gcaagctcaa tgtgaagaag   600
gaaaaatggc agcagggaaa cacgttcacg tgttctgtgc tgcatgaagg cctgcacaac   660
```
caccatactg agaagagtct ctcccactcc cccggt 696

<210> SEQ ID NO 50
<211> LENGTH: 124
<212> TYPE: DNA
<213> ORGANISM: Mus musculus

<400> SEQUENCE: 50
aaagagcctc ctccatccac tgtctccaac atggcgaccg ttgctgttct ggttgtcctt 60
ggagctgcaa tagtcactgg agctgtggtg gcttttgtga tgaagatgag aaggagaaac 120
acag 124

<210> SEQ ID NO 51
<211> LENGTH: 178
<212> TYPE: DNA
<213> ORGANISM: Mus musculus

<400> SEQUENCE: 51
gtaggaaagg gcagagtctg agttttctct cagcctcctt tagagtgtgc tctgctcatc 60
aatggggaac acaggcacac cccacattgc tactgtctct aactgggtct gctgtcagtt 120
ctgggaactt cctagtgtca agatcttcct ggaactctca cagcttttct tctcacag 178

<210> SEQ ID NO 52
<211> LENGTH: 33
<212> TYPE: DNA
<213> ORGANISM: Mus musculus

<400> SEQUENCE: 52
gtggaaaagg agggactat gctctggctc cag 33

<210> SEQ ID NO 53
<211> LENGTH: 172
<212> TYPE: DNA
<213> ORGANISM: Mus musculus

<400> SEQUENCE: 53
gttagtgtgg ggacagagtt gtcctgggga cattggagtg aagttggaga tgatgggagc 60
tctgggaatc cataatagct cctccagaga atcttctag gtgcctgagt tgtgccatga 120
aatgaatatg tacatgtaca tatgcatata catttgtttt gttttaccct ag 172

<210> SEQ ID NO 54
<211> LENGTH: 83
<212> TYPE: DNA
<213> ORGANISM: Mus musculus

<400> SEQUENCE: 54
gctcccagac ctctgatctg tctctcccag attgtaaagg tgacactcta gggtctgatt 60
ggggaggggc aatgtggaca tga 83

<210> SEQ ID NO 55
<211> LENGTH: 20
<212> TYPE: PRT
<213> ORGANISM: Homo sapiens

<400> SEQUENCE: 55

Met Glu Ser Gln Thr Gln Val Leu Met Phe Leu Leu Leu Trp Val Ser
1               5                   10                  15

Gly Ala Cys Ala
            20

<210> SEQ ID NO 56
<211> LENGTH: 108
<212> TYPE: PRT
<213> ORGANISM: Homo sapiens

<400> SEQUENCE: 56

Asp Ile Gln Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Asp Glu Tyr Pro Phe
                85                  90                  95

Thr Phe Gly Ser Gly Thr Lys Leu Glu Ile Lys Arg
            100                 105

<210> SEQ ID NO 57
<211> LENGTH: 116
<212> TYPE: PRT
<213> ORGANISM: Homo sapiens

<400> SEQUENCE: 57

Gln Val Gln Leu Lys Glu Ser Gly Pro Gly Leu Val Gln Pro Ser Gln
1               5                   10                  15

Thr Leu Ser Leu Thr Cys Thr Val Ser Gly Leu Ser Leu Ile Ser Tyr
            20                  25                  30

Gly Val Ser Trp Ala Arg Gln Pro Pro Gly Lys Gly Leu Glu Trp Ile
        35                  40                  45

Ala Ala Ile Ser Ser Gly Gly Ser Thr Tyr Tyr Asn Ser Val Leu Thr
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Glu Leu Trp Asp Tyr Tyr Asp Tyr Trp Gly Gln Gly Val Met Val
            100                 105                 110

Thr Val Ser Ser
        115

<210> SEQ ID NO 58
<211> LENGTH: 232
<212> TYPE: PRT
<213> ORGANISM: Rattus rattus

<400> SEQUENCE: 58

Ala Glu Thr Thr Ala Pro Arg Asn Pro Gly Gly Asp Cys Lys Pro Cys
1               5                   10                  15

Ile Cys Thr Gly Ser Glu Val Ser Ser Val Phe Ile Phe Pro Pro Lys
            20                  25                  30

Pro Lys Asp Val Leu Thr Ile Thr Leu Thr Pro Lys Val Thr Cys Val
            35                  40                  45

```
Val Val Asp Ile Ser Gln Asp Pro Glu Val His Phe Ser Trp Phe
    50              55                  60

Val Asp Asp Val Glu Val His Thr Ala Gln Thr Arg Pro Pro Glu Glu
65              70                  75                  80

Gln Phe Asn Ser Thr Phe Arg Ser Val Ser Glu Leu Pro Ile Leu His
                85                  90                  95

Gln Asp Trp Leu Asn Gly Arg Thr Phe Arg Cys Lys Val Thr Ser Ala
                100                 105                 110

Ala Phe Pro Ser Pro Ile Glu Lys Thr Ile Ser Lys Pro Glu Gly Arg
                115                 120                 125

Thr Gln Val Pro His Val Tyr Thr Met Ser Pro Thr Lys Glu Glu Met
            130                 135                 140

Thr Gln Asn Glu Val Ser Ile Thr Cys Met Val Lys Gly Phe Tyr Pro
145                 150                 155                 160

Pro Asp Ile Tyr Val Glu Trp Gln Met Asn Gly Gln Pro Gln Glu Asn
                165                 170                 175

Tyr Lys Asn Thr Pro Pro Thr Met Asp Thr Asp Gly Ser Tyr Phe Leu
                180                 185                 190

Tyr Ser Lys Leu Asn Val Lys Lys Glu Lys Trp Gln Gln Gly Asn Thr
            195                 200                 205

Phe Thr Cys Ser Val Leu His Glu Gly Leu His Asn His His Thr Glu
            210                 215                 220

Lys Ser Leu Ser His Ser Pro Gly
225                 230

<210> SEQ ID NO 59
<211> LENGTH: 79
<212> TYPE: PRT
<213> ORGANISM: Mus musculus

<400> SEQUENCE: 59

Lys Glu Pro Pro Pro Ser Thr Val Ser Asn Met Ala Thr Val Ala Val
1               5                   10                  15

Leu Val Val Leu Gly Ala Ala Ile Val Thr Gly Ala Val Val Ala Phe
                20                  25                  30

Val Met Lys Met Arg Arg Arg Asn Thr Gly Gly Lys Gly Gly Asp Tyr
            35                  40                  45

Ala Leu Ala Pro Gly Ser Gln Thr Ser Asp Leu Ser Leu Pro Asp Cys
            50                  55                  60

Lys Gly Asp Thr Leu Gly Ser Asp Trp Gly Gly Ala Met Trp Thr
65                  70                  75
```